US009829459B2

(12) United States Patent
Zhu et al.

(10) Patent No.: US 9,829,459 B2
(45) Date of Patent: *Nov. 28, 2017

(54) ELECTROCHEMICAL TEST SENSOR AND METHOD OF FORMING THE SAME

(71) Applicant: Bayer HealthCare LLC, Whippany, NJ (US)

(72) Inventors: Boru Zhu, Granger, IN (US); Herbert Henley, Jr., South Bend, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/076,430

(22) Filed: Nov. 11, 2013

(65) Prior Publication Data

US 2014/0061045 A1 Mar. 6, 2014

Related U.S. Application Data

(63) Continuation of application No. 12/316,157, filed on Dec. 10, 2008, now Pat. No. 8,609,180.

(Continued)

(51) Int. Cl.

*B05D 5/12* (2006.01)
*C12Q 1/00* (2006.01)

(Continued)

(52) U.S. Cl.

CPC ....... *G01N 27/3271* (2013.01); *B05C 5/0225* (2013.01); *C12Q 1/004* (2013.01);

(Continued)

(58) Field of Classification Search

CPC ......... C12C 1/001; C12C 1/004; C12C 1/005; C12C 1/006; G01N 27/3271; G01N 27/3272; G01N 33/558

(Continued)

(56) References Cited

U.S. PATENT DOCUMENTS

| | | |
|---|---|---|
| 4,545,382 A | 10/1985 | Higgins et al. |
| 4,711,245 A | 12/1987 | Higgins et al. |

(Continued)

FOREIGN PATENT DOCUMENTS

| | | |
|---|---|---|
| EP | 1650560 A1 | 4/2006 |
| EP | 1 293 574 B1 | 11/2007 |

(Continued)

OTHER PUBLICATIONS

Written Opinion corresponding to International Patent Application Serial No. PCT/US2008/086178, European Patent Office, dated Mar. 11, 2009, 7 pages.

(Continued)

*Primary Examiner* — Alex Efta

(74) *Attorney, Agent, or Firm* — Nixon Peabody LLP

(57) ABSTRACT

A method of depositing reagent on an electrochemical test sensor adapted to determine information relating to an analyte includes providing a base and forming an electrode pattern on the base. The method further includes depositing the reagent on at least the electrode pattern using a reagent-dispensing system. The reagent-dispensing system applies mechanical force to the reagent in the reagent-dispensing system to assist in providing a wet reagent droplet on at least the electrode pattern.

20 Claims, 11 Drawing Sheets

Related U.S. Application Data

(60) Provisional application No. 61/198,084, filed on Nov. 3, 2008, provisional application No. 61/007,095, filed on Dec. 10, 2007.

(51) Int. Cl.

| | |
|---|---|
| ***A61F 13/15*** | (2006.01) |
| ***G01N 27/327*** | (2006.01) |
| ***B05C 5/02*** | (2006.01) |
| *G01N 27/12* | (2006.01) |

(52) U.S. Cl.
CPC ......... *C12Q 1/006* (2013.01); *G01N 27/3272* (2013.01); *G01N 27/128* (2013.01)

(58) Field of Classification Search
USPC .............................................. 156/278; 427/58
See application file for complete search history.

(56) References Cited

U.S. PATENT DOCUMENTS

| | | | | |
|---|---|---|---|---|
| 4,863,016 | A | 9/1989 | Fong et al. | |
| 4,941,308 | A | 7/1990 | Grabenkort et al. | |
| 5,120,420 | A * | 6/1992 | Nankai et al. | 204/403.11 |
| 5,206,147 | A | 4/1993 | Hoenes | |
| 5,212,092 | A | 5/1993 | Jackson et al. | |
| 5,236,567 | A | 8/1993 | Nanba et al. | |
| 5,466,575 | A | 11/1995 | Cozzette et al. | |
| 5,512,159 | A * | 4/1996 | Yoshioka et al. | 204/403.08 |
| 5,627,075 | A * | 5/1997 | Bateson | 436/8 |
| 5,658,443 | A | 8/1997 | Yamamoto et al. | |
| 5,759,364 | A * | 6/1998 | Charlton et al. | 204/403.14 |
| 6,071,391 | A * | 6/2000 | Gotoh et al. | 204/403.05 |
| 6,261,367 | B1 | 7/2001 | Donges | |
| 6,656,702 | B1 * | 12/2003 | Yugawa et al. | 435/26 |
| 7,163,616 | B2 * | 1/2007 | Vreeke et al. | 205/777.5 |
| 2001/0024804 | A1 | 9/2001 | Shen | |
| 2003/0146110 | A1 * | 8/2003 | Karinka et al. | 205/777.5 |
| 2003/0152994 | A1 * | 8/2003 | Woudenberg | B01L 3/50273 435/6.12 |
| 2004/0072364 | A1 * | 4/2004 | Tisone | B01J 19/0046 436/180 |
| 2005/0152946 | A1 * | 7/2005 | Hunter et al. | 424/423 |
| 2005/0230252 | A1 | 10/2005 | Tsai et al. | |
| 2006/0157517 | A1 | 7/2006 | Fiske et al. | |
| 2007/0000776 | A1 | 1/2007 | Karube et al. | |
| 2008/0199937 | A1 | 8/2008 | Chu et al. | |

FOREIGN PATENT DOCUMENTS

| | | | |
|---|---|---|---|
| JP | 63-144246 | A | 6/1988 |
| JP | 2000-516526 | A | 12/2000 |
| JP | 2002-500098 | A | 1/2002 |
| JP | 2003-107031 | A | 4/2003 |
| JP | 2003-185619 | | 7/2003 |
| JP | 2005-233917 | A | 9/2005 |
| JP | 2006275818 | A | 10/2006 |
| JP | 2007-524816 | | 8/2007 |
| JP | 2008-532047 | A | 8/2008 |
| JP | 4913355 | B2 | 4/2012 |
| WO | WO 98/04358 | A1 | 2/1998 |
| WO | WO 2004113917 | A2 * | 12/2004 |
| WO | WO 2006057722 | A1 | 6/2006 |
| WO | WO 2006/096619 | A2 | 9/2006 |
| WO | WO 2007/022215 | A2 | 2/2007 |

OTHER PUBLICATIONS

International Search Report corresponding to International Patent Application Serial No. PCT/US2008/086178, European Patent Office, dated Mar. 11, 2009, 4 pages.

* cited by examiner

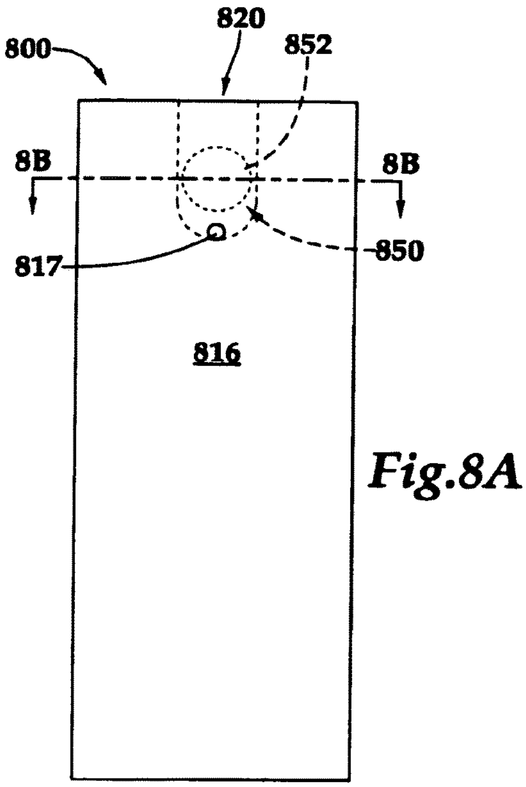
Fig.8A
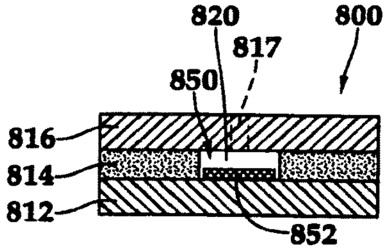
Fig.8B
Fig.9
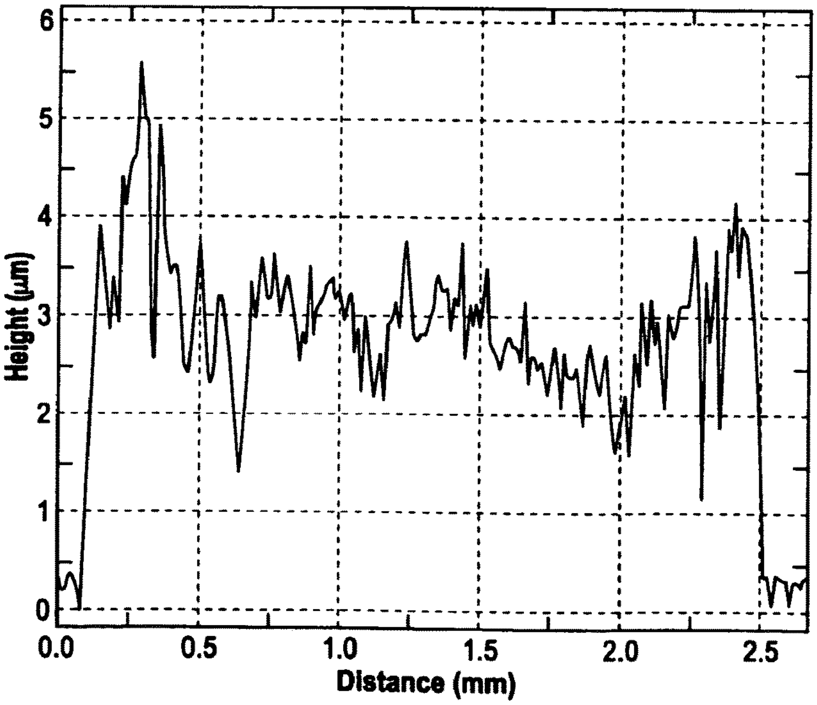

ELECTROCHEMICAL TEST SENSOR AND METHOD OF FORMING THE SAME

CROSS REFERENCE TO RELATED APPLICATIONS

This application is a continuation of prior application Ser. No. 12/316,157, filed Dec. 10, 2008, now allowed, which claims priority to and the benefit of U.S. Provisional Application No. 61/007,095, filed Dec. 10, 2007, and U.S. Provisional Application No. 61/198,084, filed Nov. 3, 2008, each of which is hereby incorporated by reference herein in its entirety.

FIELD OF THE INVENTION

The present invention relates generally to methods of depositing reagent on a surface. More specifically, the present invention relates to methods of depositing a wet reagent droplet on an electrode pattern in a test sensor.

BACKGROUND OF THE INVENTION

The quantitative determination of analytes in body fluids is of great importance in the diagnoses and maintenance of certain physical conditions. For example, blood glucose, hemoglobin (Hb), hemoglobin $A1_c$ ($HbA1_c$), lactate, cholesterol, bilirubin, and other analytes should be monitored in certain individuals. Individuals with low blood glucose levels may need medical attention. In particular, it is important that individuals who have diabetics frequently check the glucose level in their body fluids because such individuals may become ill if their blood glucose level becomes too high—a condition known as hyperglycemia. The results of these analyte tests may be used to determine what, if any, insulin or other medication should be administered.

The analyte concentration tests are typically performed using optical or electrochemical testing methods. In the embodiments employing an electrochemical method, a test sensor contains biosensing or a dry reagent layer that reacts with, for example, blood glucose. A testing portion of the test sensor contains the dry reagent layer and is adapted to receive a fluid (e.g., blood) being tested that has accumulated on, for example, a person's finger after the finger has been pricked. The fluid is typically drawn into a channel that extends from an end or side of the test sensor to at least the dry reagent layer, located in the testing portion. In, certain embodiments, the test sensor draws the fluid into the channel using capillary action so that a sufficient amount of fluid to be tested is drawn into the test sensor's testing portion. The fluid then chemically reacts with the dry reagent layer in the testing portion. This results in an electrical signal, indicative of the glucose level in the fluid, being supplied to electrical contact areas, which are typically located at a second opposing end near the rear or contact portion of the test sensor.

The test sensor's accuracy and precision depend on the uniform consistency of the dry reagent layer's physical structure and chemical composition. To ensure good precision and accuracy, from test sensor to test sensor, the dry reagent layer should have little variation not only in quantity, but also in physical structure. Thus, it is desirable for the reagent material to be deposited as a wet reagent droplet having substantially uniform height, radius, and contact angle from test sensor to test sensor such that when the wet reagent droplet dries a dry reagent layer is formed. However, the wet reagent droplet is typically deposited on a conductive-covered polymeric substrate (e.g., a gold PET substrate). Such substrate surfaces tend to always contain surface variations or surface irregularities. These surface variations may be caused by contamination on the deposition surface, irregularities of the electrode pattern surface, or irregularities of the polymeric substrate, which all make it difficult to deposit a structurally uniform wet reagent droplet from test sensor to test sensor.

It would be desirable to overcome the above-noted problem of surface variations, while providing a precise, rapid, and accurate method of depositing uniform wet reagent droplets from test sensor to test sensor.

SUMMARY OF THE INVENTION

According to one embodiment, a method of depositing reagent on an electrochemical test sensor adapted to determine information relating to an analyte includes providing a base and forming an electrode pattern on the base. The method further includes depositing the reagent on at least the electrode pattern using a reagent-dispensing system. The reagent-dispensing system applies mechanical force to the reagent in the reagent-dispensing system to assist in providing a wet reagent droplet on at least the electrode pattern.

According to another embodiment, a method of forming an electrochemical test sensor adapted to determine information relating to an analyte includes providing a base, forming an electrode pattern on the base, and providing a reagent-dispensing system. The reagent-dispensing system deposits reagent on at least the electrode pattern. The reagent-dispensing system includes a compression member, a piston-needle assembly, an air chamber, a fluid chamber, a nozzle, and a body. The compression member has a compression adjustment mechanism that may be used to adjust the amount of compression on the compression member. The piston-needle assembly has a closed position and an open position. The method further includes supplying the reagent into the fluid chamber. The fluid chamber has a fluid input and a fluid output. The fluid output has an open position and a closed position that correspond to the open and closed positions of the piston-needle assembly. The method further includes supplying pressurized air to the air chamber to cause the piston-needle assembly to compress the compression member. While supplying the pressurized air, the piston-needle assembly is in the open position, and the fluid output is in the open position. The method further includes releasing the supplied pressurized air from the air chamber to allow the compression member to force the piston-needle assembly into the closed position. The piston-needle assembly mechanically forces a portion of the reagent in the fluid chamber out of the nozzle, and the portion of the reagent is deposited on at least the electrode pattern as a wet reagent droplet.

According to another embodiment, a method of forming an electrochemical test sensor adapted to determine information relating to an analyte includes providing a base, forming an electrode pattern on the base, and providing a reagent-dispensing system for depositing reagent on at least the electrode pattern. The reagent-dispensing system includes a solenoid control valve, a plunger, a compression member, and a nozzle. The nozzle has an output diameter, and the solenoid control valve has an open and a closed position. The method further includes supplying pressurized reagent, and opening the control valve of the reagent-dispensing system to cause the supplied pressurized reagent to be dispensed through the nozzle and deposited on at least the electrode pattern as a wet reagent droplet.

According to another embodiment, a method of forming an optical test sensor adapted to determine information relating to an analyte includes providing a base and providing a reagent-dispensing system for depositing reagent on the base. The reagent-dispensing system includes a solenoid control valve, a plunger, a compression member, and a nozzle. The nozzle has an output diameter, and the solenoid control valve has an open and a closed position. The method further includes supplying pressurized reagent and opening the control valve of the reagent-dispensing system to cause the supplied pressurized reagent to be dispensed through the nozzle and deposited on the base as a wet reagent droplet. The method further includes drying the wet reagent droplet to form a dry reagent layer, providing a lid, and attaching the lid to the base to assist in forming a channel in the test sensor. The channel assists in allowing a fluid sample to contact the dry reagent layer located on the base.

According to another embodiment, an electrochemical test sensor comprises a base, a lid, a plurality of electrodes and a dried reagent. The dried reagent includes an enzyme, a mediator, and a sufficient amount of a multivalent salt such that dried reagent has a uniformity in which the ratio of the thinnest point to the thickest point is greater than about 0.2.

According to another method, an electrochemical test sensor is formed. A base and a lid are provided. A plurality of electrodes is formed on at least one of the base and the lid. Reagent solution is placed so as to be in contact with at least one of the electrodes. The reagent solution includes an enzyme, a mediator, and a multivalent salt. The multivalent salt has a concentration greater than 40 mM in the reagent solution. The reagent solution is dried after placement thereof.

According to a further method, an electrochemical test sensor is formed. A base and a lid are provided. A plurality of electrodes is formed on at least one of the base and the lid. Reagent solution is placed so as to be in contact with at least one of the electrodes. The reagent solution includes an enzyme, a mediator, and an electrolyte. The electrolyte is at least 0.1 wt. % of the reagent solution. The reagent solution is dried after placement thereof.

BRIEF DESCRIPTION OF THE DRAWINGS

FIG. 8*a* is a top view of another test sensor having a reagent droplet.

FIG. 8*b* is a cross-sectional view of the test sensor of FIG. 8*a* taken generally along line 8B-8B of FIG. 8*a*.

FIGS. 9-13 are plots of reagent height versus distance in Examples 1-5 discussed below to illustrate the uniformity of the reagent sample.

Figure 1A:
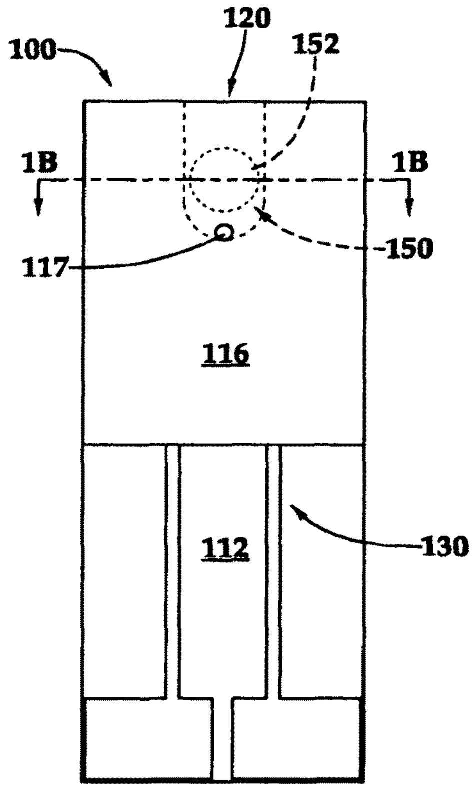
FIG. 1*a* is a top view of a test sensor having a reagent droplet.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF ILLUSTRATED EMBODIMENTS

The present invention is directed to methods of depositing a wet reagent droplet on a surface. Specifically, the present invention is directed to methods of depositing a wet reagent droplet on, for example, an electrode pattern formed on a base of a test sensor used in determining information related to an analyte of a fluid sample taken from a user. Moreover, this invention is directed to certain methods of using reagent-dispensing systems to deposit a plurality of wet reagent droplets of substantially uniform structure from test sensor to test sensor. The uniformity of the wet reagent droplets produce substantially uniform dry reagent layers from test sensor to test sensor that increase the precision and accuracy of the information related to an analyte of the fluid sample.

A test sensor is typically adapted to receive a fluid sample, which an instrument or meter subsequently analyzes to produce a concentration reading. Analytes that may be measured include glucose, lipid profiles (e.g., cholesterol, triglycerides, LDL, and HDL), microalbumin, hemoglobin $A_{1C}$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid), creatinine, urea, urine, and non-body fluids.

The test sensors may be electrochemical test sensors. The electrochemical test sensors include at least a base (also referred to as a substrate), an electrode pattern on the base, a dry reagent layer, and a second layer such as a lid and/or a spacer. In one embodiment, the electrochemical test sensors include a base, an electrode pattern, a dry reagent layer, and a lid. In another embodiment, the electrochemical test sensors include a base, an electrode pattern, a spacer, a dry reagent layer, and a lid.

The base, the spacer, and the lid may be made from a variety of materials such as polymeric materials. Non-limiting examples of polymeric materials that may be used to form the base, the spacer, and the lid include polycarbonate, polyethylene terephthalate (PET), polystyrene, polyimide, and combinations thereof. It is contemplated that the base, the spacer, and the lid may be independently made of other materials. The electrode pattern on the base may be made from a variety of conductive materials including, but not limited to, carbon, gold, platinum, ruthenium, rhodium, palladium or combinations thereof. The electrode pattern may also include test-sensor contacts and conductive leads. The test-sensor contacts electrically connect the electrodes via the leads to a meter for analysis.

Figure 1C:
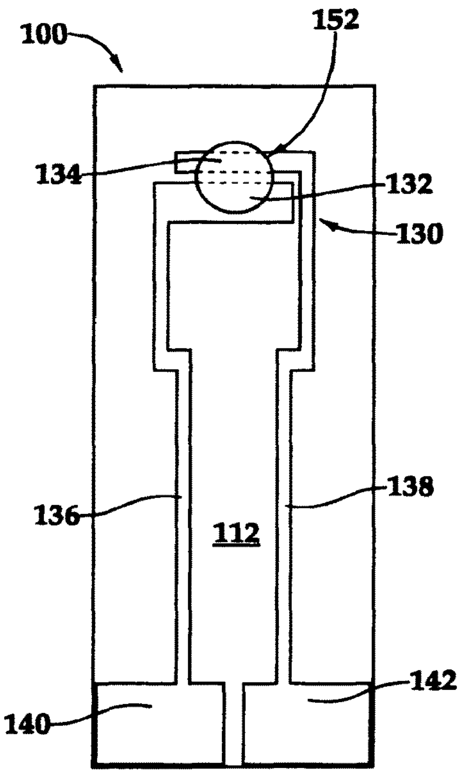
FIG. 1*c* is a top view of the test sensor of FIG. 1*a* having its lid removed.
Figure 1B:
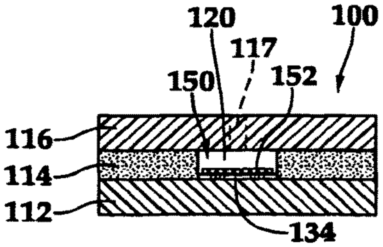
FIG. 1*b* is a cross-sectional view of the test sensor of FIG. 1*a* taken generally along line 1B-1B of FIG. 1*a*.

One non-limiting example of an electrochemical test sensor is shown in FIGS. 1*a-c*. FIGS. 1*a,b* depict an electrochemical test sensor 100 that includes a base 112, a spacer 114, an electrode pattern 130, a testing portion 150, and a lid 116. FIG. 1*a* depicts the test sensor 100 with the lid 116 attached. To form the test sensor 100, the base 112, the spacer 114, and the lid 116 are attached by, for example, an adhesive or heat sealing. A channel 120 (e.g., capillary channel) is formed when the base 112, the spacer 114, and the lid 116 are attached to each other. According to one method, a user introduces a fluid sample (e.g., blood) into the channel 120 that eventually reaches the testing portion 150. The testing portion 150 includes at least two electrodes and a dry reagent layer 152. The lid 116 may include a vent 117 to assist the flow of the fluid sample into the channel 120.

The enzyme is selected to react with the desired analyte or analytes to be tested so as to assist in determining information related to an analyte of the fluid sample. The dry reagent layer 152 converts an analyte of interest (e.g., glucose) in the fluid sample (e.g., blood) into a chemical species that is electrochemically measurable, in terms of the electrical current it produces, by the components of the electrode pattern 130.

FIG. 1*c* depicts the test sensor 100 of FIG. 1*a* with the lid 116 completely removed to show the electrode pattern 130 on the base 112. The electrode pattern 130 includes a plurality of electrodes 132 and 134, a plurality of conductive leads or traces 136, 138, and a plurality of test-sensor contacts 140, 142. The plurality of electrodes 132, 134 includes at least a counter electrode 132 and a working electrode 134. The working electrode measures the current when a potential is applied across the working and counter electrodes. The counter electrode should be sufficiently large so as to support the reaction occurring at the working electrode. The applied voltage may be referenced to the dry reagent droplet 152 deposited on the electrodes 132, 134. It is contemplated that the test sensor 100 may include other electrodes such as a trigger electrode, a detection electrode, a hematocrit electrode, or a second working electrode. It is also contemplated that the dry reagent layer 152 may be formed on the counter electrode 132, the working electrode 134, the base 112, or any combination thereof.

The electrodes are formed of conductive materials such as, for example, metallic materials (e.g., gold, platinum, palladium, rhodium, ruthenium, or combinations thereof) or carbon.

Figure 2A:
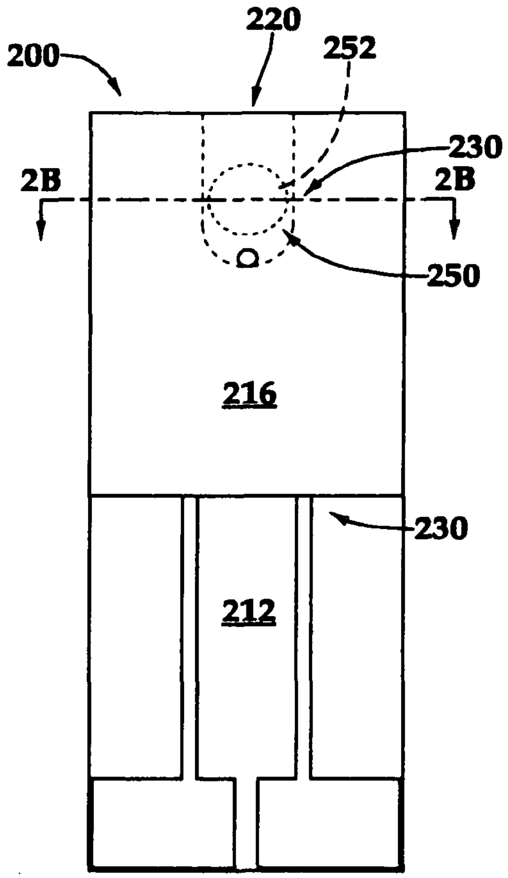
FIG. 2*a* is a top view of another test sensor having a reagent droplet.
Figure 2B:
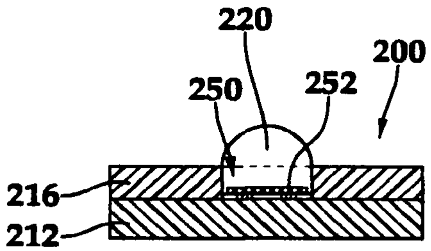
FIG. 2*b* is a cross-sectional view of the test sensor of FIG. 2*a* taken generally along line 2B-2B of FIG. 2*a*.

Another non-limiting example of an electrochemical test sensor is shown in FIGS. 2*a,b*. FIGS. 2*a,b* depict an electrochemical test sensor 200 that includes a base 212, an electrode pattern 230, a testing portion 250, and a lid 216. The base 212 may be the same or similar to the base 112 discussed above. The lid 216 may be formed with a convex opening that is adapted to receive a fluid sample. FIG. 2*a* depicts the base 212 with the lid attached. A channel 220 (e.g., capillary channel) is formed when the base 212 and the lid 216 are attached to each other. According to one method, a user may introduce the fluid sample into the channel 220 such that the fluid sample reaches the testing portion 250. The testing portion 250 includes at least two electrodes and a dry reagent layer 252. The dry reagent layer 252 may include an enzyme similar to or the same as the enzyme included in the dry reagent layer 152 of FIG. 1*a*.

The electrode pattern 230 formed on the base 212 may be the same or similar to the electrode pattern 130 described above. Similarly, the electrodes include a counter and working electrode in one embodiment. In other embodiments, the electrodes may include additional electrodes such as a trigger electrode, a detection electrode, a hematocrit electrode, a second working electrode, and other electrodes.

Figure 3A:
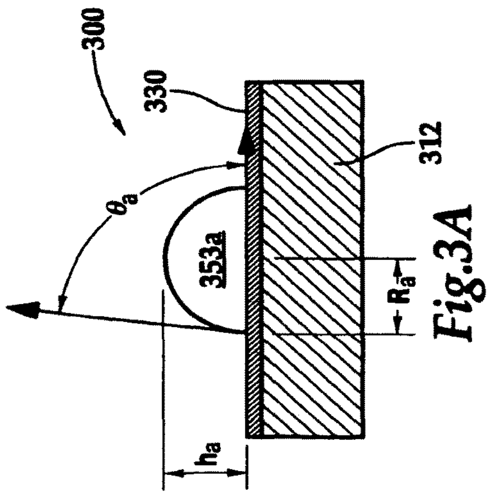
FIG. 3*a* is a cross-sectional side view of a portion of another test sensor having a wet reagent droplet.

Now referring to FIGS. 3*a*-3*d*, a portion of an electrochemical test sensor is shown. FIG. 3*a* depicts a cross-sectional view of a very hydrophobic portion of an electrochemical test sensor 300 that includes a base 312, an electrode pattern 330, and a wet reagent droplet 353*a*. The base 312 and the electrode pattern 330 are the same as, or similar to, the base 112 and the electrode pattern 130 described above in relation to the test sensor 100.

According to some embodiments, the wet reagent droplet 353 has at least three physical parameters: height ($h_a$), radius ($R_a$), and contact angle ($e_a$). These parameters ($h_a$, $R_a$, and $\theta_a$) can define the physical structure of the wet reagent droplet 353*a* in terms of uniformity from test sensor to test sensor when the wet reagent droplet 353*a* is deposited. The height $h_a$ and radius $R_a$ are functions of the contact angle $\theta_a$. As the contact angle $\theta_a$ decreases, the height $h_a$ decreases and the radius $R_a$ increases. The wet reagent droplet 353*a* may be dispensed on the base 312, the electrode pattern 330, or a combination thereof. Thus, the contact angle $\theta_a$ of the wet reagent droplet 353*a* is a function of the surface energy of a deposition surface (e.g., base 312 and/or electrode pattern 330). The surface energy of the deposition surface depends on at least the electrode pattern 330 surface, the base 312 (e.g., polymer) surface, and contamination. The electrode pattern 330 surface may contain surface irregularities due to, for example, the printing or placing process of the electrode pattern 330 on the base 312, or due to the material of the electrode pattern 330 itself. The base 312 may also contain surface irregularities due to the segments of the polymer molecules forming the base 312 that migrate with changes in the environment or temperature. These surface variation sources make deposition of a substantially uniform wet reagent droplet 353*a* from test sensor to test sensor very difficult.

According to some embodiments, the wet reagent droplet 353 physical parameters include covering area, CA. The covering area CA and the height h can be used to define the uniformity of the physical structure of the wet reagent droplets 353 and dry reagent layers from test sensor to test sensor. The covering area is equal to the footprint of the wet reagent droplet 353. Put another way, the covering area is the physical area of the wet reagent droplet 353 that covers the base 312 and/or the electrode pattern 330. The covering area is generally circular, although other shapes and sizes of covering area are contemplated, such as, for example, oval, square, elliptical, oblong, etc.

The covering area of the wet reagent droplet 353 is a function of the surface energy of the deposition surface (e.g., base 312 and/or electrode pattern 330) and an applied mechanical energy or force (described below). More surface irregularities and surface contamination on the deposition surface will reduce the covering area and increase the height h. Larger mechanical forces applied to the reagent while dispensing wet reagent droplets 353 will increase the covering area and reduce the height h.

Figure 3B:
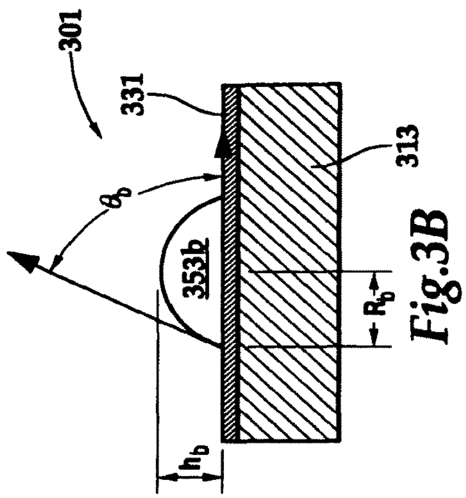
FIG. 3*b* is a cross-sectional side view of a portion of another test sensor having a wet reagent droplet.

Referring to FIG. 3*b*, a cross-sectional view of a very hydrophilic portion of an electrochemical test sensor 301 is shown. The test sensor 301 includes a base 313, an electrode pattern 331, and a wet reagent droplet 353*b*. The base 313 and the electrode pattern 331 are the same or similar to the base 112 and the electrode pattern 130 described above in relation to the test sensor 100. The test sensor 301 depicts the wet reagent droplet 353*b* with a contact angle $\theta_b$ that is smaller than the contact angle $\theta_a$ of the test sensor 300 shown in FIG. 3*a*. The smaller contact angle $\theta_b$ of FIG. 3*b* is, for example, due to the very hydrophilic deposition surface as compared to the very hydrophobic deposition surface of FIG. 3*a*. Put another way, a deposition surface that is naturally hydrophilic will result in a wet reagent droplet with a smaller contact angle θ. The smaller contact angle $\theta_b$ also yields a greater amount of spreading of the wet reagent droplet 353*b*. The wet reagent droplets 353*a,b* were deposited with no external force and no added kinetic energy.

The present invention is directed to methods of depositing wet reagent droplets 353 with a reagent-dispensing system that adds kinetic energy to the reagent as it is being deposited. The kinetic energy applied to the reagent makes the reagent less sensitive to surface variations, which yields wet reagent droplets 353 having substantially uniform covering areas CA and heights h from test sensor to test sensor. Once the wet reagent droplet 353 is deposited, it is contemplated that the wet reagent droplet 353 will dry and form a dry reagent layer. It is also contemplated that the wet reagent droplet 353 contains 80 percent or more water that evaporates during the drying process. It is further contemplated that depositing wet reagent droplets 353 having substantially uniform covering areas CA and heights $h_1$ will yield dry reagent layers having substantially uniform covering areas CA and heights $h_2$, where $h_2$ is less than $h_1$.

Figure 3C:
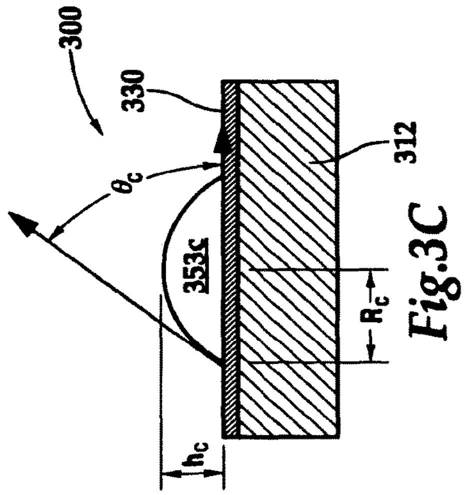
FIG. 3*c* is the test sensor of FIG. 3*a* having a wet reagent droplet deposited with kinetic energy.
Figure 3D:
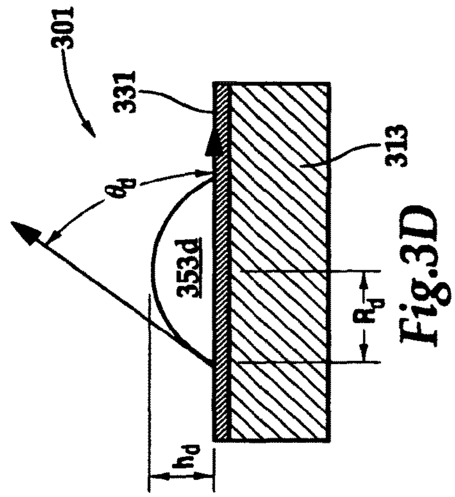
FIG. 3*d* is the test sensor of FIG. 3*b* having a wet reagent droplet deposited with kinetic energy.

Referring to FIG. 3*c*, the test sensor 300 of FIG. 3*a* is shown with a wet reagent droplet 353*c*. The wet reagent droplet 353*c* was deposited using one of the methods of the present invention, disclosed below, which adds an external force or adds kinetic energy to the regent being deposited. The wet reagent droplet 353*c* has a contact angle $\theta_c$ that is less than the contact angle $\theta_a$ of the test sensor 300 of FIG. 3*a* because of, for example, the added kinetic energy. Similarly, FIG. 3*d* depicts the test sensor 301 of FIG. 3*b* with a wet reagent droplet 353*d*. The wet reagent droplet 353*d* was also deposited using one of the methods of the present invention. The wet reagent droplet 353*d* has a contact angle $\theta_d$ that is less than the contact angle $\theta_b$ of the test sensor 301 of FIG. 3*b* because of, for example, the added kinetic energy. It is contemplated that the amount of the external force or added kinetic energy should be sufficient to make the reagent less sensitive to the surface variations. The less sensitive reagent should yield a wet reagent droplet having a contact angle θ that is equal to or less than the contact angle θ of a wet reagent droplet 353 deposited on the same deposition surface at the most hydrophilic portion. Put another way, the external force or added kinetic energy causes the deposited reagent to form a wet reagent droplet 353*c* with a contact angle $\theta_c$ equal to or less than the contact angle $\theta_b$ of a wet reagent droplet 353*b* deposited on a very hydrophilic test sensor 3θ1 without any external force or added kinetic energy.

One non-limiting example of how surface contamination affects surface energy provides: when a sessile drop of water is placed on a clean pure polished metallic (e.g., gold) surface, the water, in theory, spreads spontaneously over the metal and exhibits a zero contact angle θ. However, in practice, some hydrophilic organic or inorganic contaminates always absorb into the gold surface causing the surface to act less hydrophilic and more hydrophobic (i.e., less spreading of the water). The hydrophobic characteristics of the surface decrease the surface energy and result in an increased contact angle θ. The problem with the increased contact angle θ is that the increase is randomly based on the varying levels of uncontrollable contaminates from surface to surface at the time of dispensing.

Thus, the variations in the electrode pattern surface 330, 331, and the base surface 312,313, and the presence of contamination all result in varying amounts of spreading of the wet reagent droplet 353 from test sensor to test sensor. The varying amounts of spreading yield random contact angles θ for each of the wet reagent droplets 353 dispensed on the base 312,313 and/or the electrode pattern 330,331. The random contact angles θ produce dry reagent layers having different physical structures. These variances in dry reagent-layer structure, due to surface variations, yield less precise and less accurate testing results from test sensor to test sensor.

The present invention is directed to methods of compensating for these variances in dry reagent-layer structure by depositing the reagent using a reagent-dispensing system. According to one method, reagent is deposited on an electrochemical test sensor. The method includes providing a base and forming an electrode pattern on the base. The base and electrode pattern may be similar to or the same as the base 112 and electrode pattern 130 discussed above in reference to the test sensor 100. The reagent is deposited on at least the electrode pattern using a reagent-dispensing system. It is contemplated that the reagent may be deposited on the base, the electrode pattern, or the combination thereof.

The reagent-dispensing system applies a mechanical force to the reagent contained in the reagent-dispensing system. The mechanical force assists in providing a wet reagent droplet on the base and/or the electrode pattern. The wet reagent droplet has at least four physical parameters: covering area CA, height h, radius R, and contact angle θ. These wet reagent droplet parameters are the same as the parameters of the wet reagent droplet 353 of the test sensors 300, 301 described above.

The covering area CA, height h, radius R, and contact angle θ of the wet reagent droplet are a function of the amount of mechanical force the reagent-dispensing system exerts on the reagent. The reagent-dispensing system exerts a sufficient amount of mechanical force to overcome surface variations or contamination such that the deposited reagent forms a substantially uniform wet reagent droplet from test sensor to test sensor. The amount of mechanical force exerted on the reagent will typically vary with the viscosity of the reagent being deposited. The reagent viscosity is generally in the range of 1-100 centipoise. It is further contemplated that as the reagent viscosity increases, the amount of force should increase accordingly to maintain substantially uniform wet reagent droplets from test sensor to test sensor. Put another way, the applied force should be sufficient to deposit a wet reagent droplet with a contact angle θ that is at least equal to or less than the contact angle $\theta_b$ of the wet reagent droplet 353*b* deposited with no mechanical force on the very hydrophilic test sensor 301 of FIG. 3*b*. It is also contemplated that the mechanical force exerted on the reagent may be derived from, for example but not limited to, a spring, a piston, a motor, a solenoid, compressed air, or a hydraulic system.

In another method, the reagent-dispensing system may deposit the wet reagent droplet on a plasma-treated surface or on a non-plasma-treated surface. A variety of contaminates may be present on the base and/or on the electrode pattern when the reagent-dispensing system deposits the wet reagent droplet. It is contemplated that the contamination may be, for example, hydrophobic material, hydrophilic organic and inorganic material, or water from varying levels of humidity.

The exertion of a sufficient amount of mechanical force on the reagent provides a surprising result of depositing a wet reagent droplet having a substantially uniform structure in terms of height h, radius R, and contact angle θ, from test sensor to test sensor. Additionally, the exertion of a sufficient amount of mechanical force on the reagent provides a surprising result of depositing a wet reagent droplet having a substantially uniform covering area and height h, from test sensor to test sensor. These uniform wet reagent droplets provide dry reagent layers having substantially uniform covering area CA and height $h_2$ from test sensor to test sensor that yield more accurate, precise, consistent, and reliable testing results when using one or more test sensors with a meter for determining information relating to an analyte.

Figure 4A:
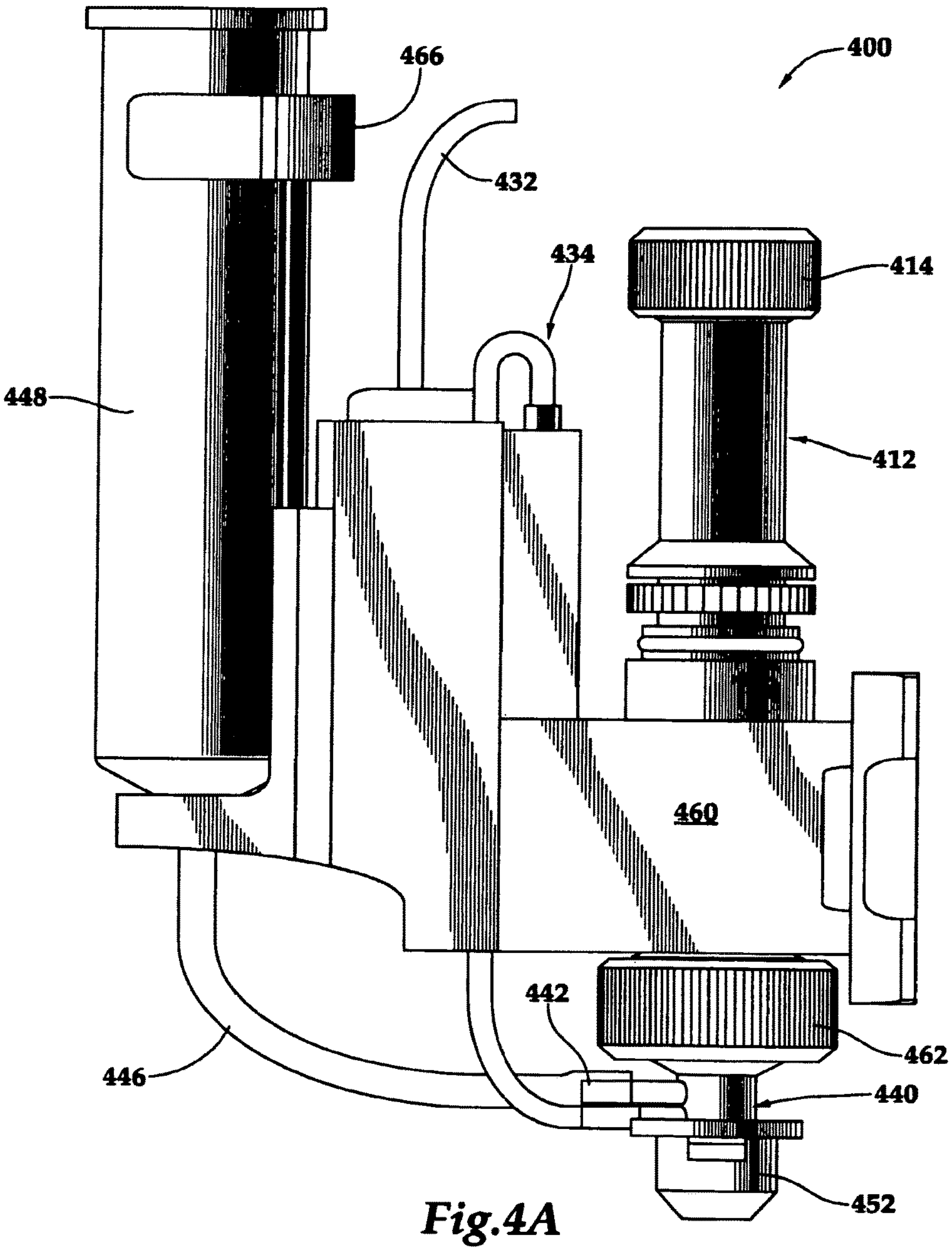
FIG. 4*a* is a front plan view of a reagent-dispensing system according to one method of the present invention.
Figure 4B:
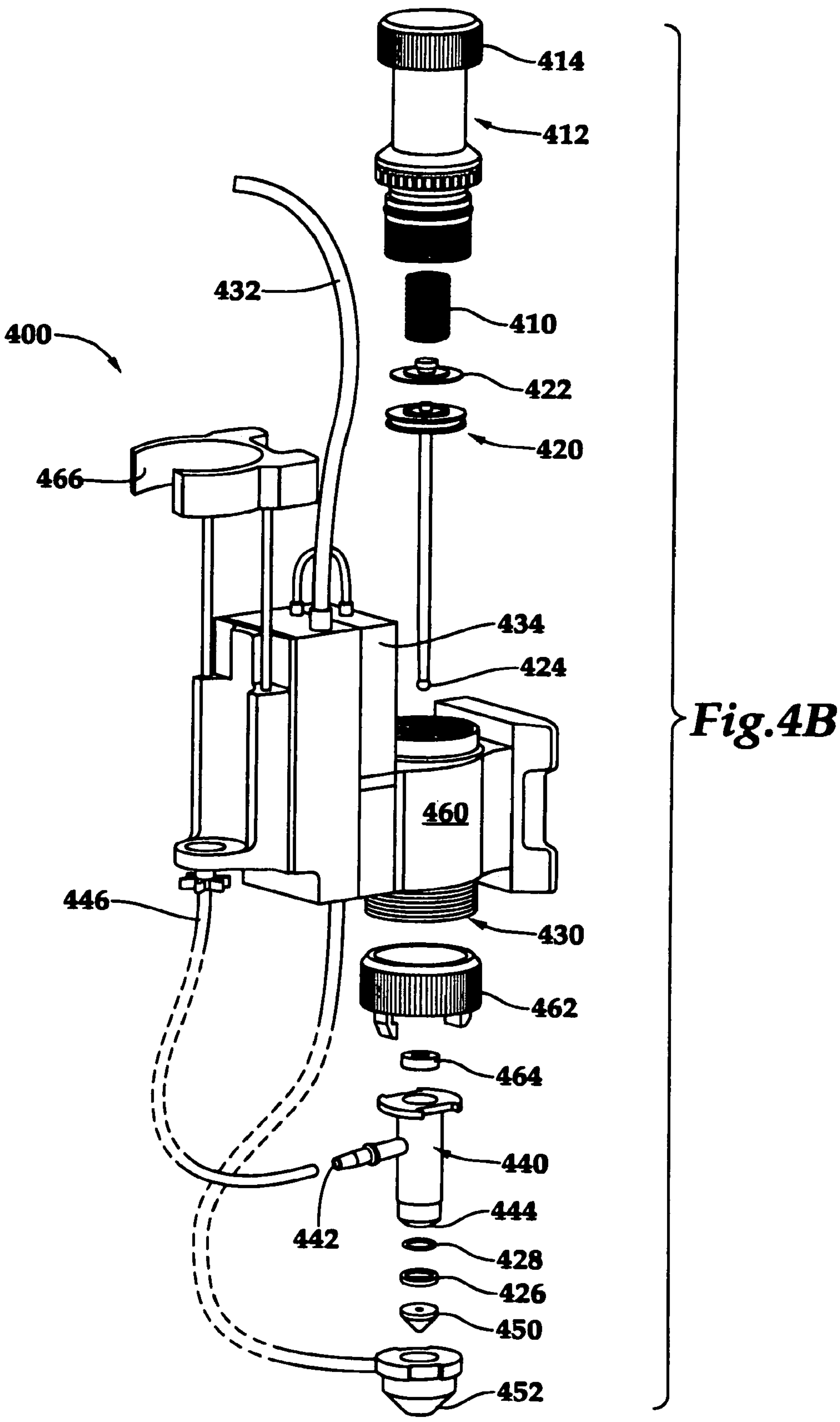
FIG. 4*b* is an exploded view of a portion of the reagent-dispensing system of FIG. 4*a*.

According to one method, an electrochemical test sensor is formed having a dry reagent layer. The test sensor may be the same or similar to the test sensors 100, 200, 300 or 301 described above. The method includes providing a base or substrate and forming an electrode pattern on the base. The base and the electrode pattern may be the same or similar to the base 112 and the electrode pattern 130 described above. A reagent-dispensing system is supplied for depositing reagent. It is contemplated that the reagent-dispensing system may deposit the reagent on the base, the electrode pattern, or the combination thereof. FIG. 4*a* depicts a front plan view of one non-limiting example of a reagent-dispensing system 400. FIG. 4*b* depicts an exploded view of the reagent-dispensing system 400 of FIG. 4*a*.

Referring to FIGS. 4*a,b*, the reagent-dispensing system 400 includes a compression member 410, a piston-needle assembly 420, an air chamber 430, a fluid chamber 440, a nozzle 450, and a body 460. The compression member 410 is connected to a compression-adjustment mechanism 412. The compression-adjustment mechanism 412 allows a user to adjust the amount of initial compression of the compression member 410. It is contemplated that the user may compress the compression member 410 by threading or screwing a top portion 414 of the compression-adjustment mechanism 412. It is also contemplated that other mechanisms may be used to compress the compression member 410. Alternatively, it is contemplated that the reagent-dispensing system may be provided without a compression-adjustment mechanism. It is contemplated that the compression member may be, for example, but not limited to, a spring.

The piston-needle assembly 420 has two opposing ends. The first opposing end contacts a load button 422. The load button 422 is connected to one side of the compression member 410 such that when the first opposing end of the piston-needle assembly 420 presses against the load button 422, the load button 422 further compresses the compression member 410. It is contemplated that the reagent-dispensing system may be provided without a load button. The second opposing end of the piston-needle assembly 420 has a ball-tip 424 that removably contacts a seat 426. The seat may further include an o-ring 428. The piston-needle assembly 420 also has a closed position and an open position. The closed position occurs when the ball-tip 424 contacts the seat 426, which inhibits or prevents the reagent from exiting the nozzle 450. The open position of the piston-needle assembly 420 occurs when the piston-needle assembly 420 compresses the compression member 410, thereby disconnecting the ball-tip 424 from the seat 426. It is contemplated that the second opposing end of the piston-needle assembly may be of other shapes and sizes than depicted in FIG. 4*b*, such as, but not limited to, a square-tip, a triangular-tip, a polygonal-tip, rounded-tip, a bullet-tip etc. It is also contemplated that the piston-needle assembly 420 may oscillate between the open and the closed positions in less than one micro-second.

The reagent is supplied into the fluid chamber 440 having a fluid input 442 and a fluid output 444. A feed tube 446 connects the fluid input 442 to a fluid reservoir 448 depicted in FIG. 4*a*. The fluid reservoir 448 may be attached to the reagent-dispensing system body 460 via a reservoir clip 466 such as shown in FIG. 4*b*. It is contemplated that the fluid reservoir may be stored in a separate location and not be attached to the body 460. The fluid output 444 may attach to the seat 426 via the o-ring 428. The fluid chamber 440 attaches to the reagent-dispensing system body 460 via a collar 462 and a seal 464. The fluid output 444 has an open position and a closed position that corresponds with the open and closed positions of the piston-needle assembly 420. Only when the piston-needle assembly 420 is in the open position may the reagent exit the fluid output 444.

It is contemplated that the fluid reservoir may further include an external source of air pressure for maintaining a fluid pressure. It is contemplated that the fluid pressure may generally be from about 1 to about 30 psi, which corresponds to a reagent having a viscosity of from about 1 to about 100 centipoise. It is desirable to have a reagent viscosity of from about 2 to about 10 centipoise with the fluid pressure being from about 2 to about 5 psi. Other levels of fluid pressure are contemplated. It is further contemplated that the required fluid pressure may be supplied by the fluid itself, in which the fluid reservoir 448 is a fluid column of sufficient height. It is contemplated that the fluid column having a height of from about 5 to about 8 feet would likely supply the desired fluid pressure.

Pressurized air is supplied to the air chamber 430. An air supply tube 432 connects an exterior source of the pressurized air to a solenoid valve 434 (FIG. 4*a*). An electrical signal triggers the solenoid valve 434 to allow the pressurized air into the air chamber 430. The pressurized air applies a force to the piston-needle assembly 420 to compress the compression member 410 further. The amount of secondary compression of the compression member 410 depends on how much initial compression the user applied to the compression member 410 via the compression-adjustment mechanism 412. A greater amount of initial compression reduces the available amount of secondary compression.

The pressurized air also forces the piston-needle assembly 420 to lift the ball-tip 424, thereby moving the piston-needle assembly 420 into the open position. As the ball-tip 424 is lifted from the seat 426, the reagent is allowed to flow down and around the ball-tip 424 of the piston-needle assembly 420. The electrical signal is then terminated, which discharges the solenoid valve 434, thereby releasing the pressurized air from the air chamber 430. The compression member 410 may then force or slam the ball-tip 424 back into contact with the seat 426, thereby ejecting a portion of the reagent from the nozzle 450. The ejected reagent is then deposited on the base and/or the electrode pattern as a wet reagent droplet having one or more structural parameters including covering area CA, height h, radius R, and contact angle θ.

It is contemplated that varying amounts of secondary compression may be used to eject the portion of the reagent. It is also contemplated that a lower amount of secondary compression results in a smaller amount of force applied to the portion of reagent. However, the exertion of a sufficient amount of secondary compression will eject the portion of the reagent such that the ejected reagent is less surface sensitive and is deposited on the base and/or electrode pattern as a wet reagent droplet having substantially uniform parameters (CA, h, R, and θ) from test sensor to test sensor. This uniform wet reagent droplet dries to provide a dry reagent layer that yields more accurate, precise, and reliable test results when using a test sensor with a meter for determining information relating to an analyte. It is contemplated that a thermal control assembly 452 may be attached to the nozzle 450. The thermal control assembly 452 may be used to monitor and/or vary the temperature of the reagent exiting the nozzle 450.

According to another method, an electrochemical test sensor is formed having a dry reagent layer. The test sensor may be the same or similar to the test sensors 100, 200, 300 or 301 described above. The method includes providing a base or substrate, forming an electrode pattern on the base, depositing a wet reagent droplet on at least the electrode pattern, drying the wet reagent droplet to form the dry reagent layer, providing a lid, and attaching the lid to the base. It is contemplated that a spacer may be provided similar to the spacer 114 described above in relation to the test sensor 100. The base, the electrode pattern, and the lid may be the same or similar to the base 112, the electrode pattern 130, and the lid 116 described above and shown in FIG. 1*a*. It is contemplated that the reagent is deposited on the base, the electrode pattern, or a combination thereof using the same or similar reagent-dispensing system as the reagent-dispensing system 400 described above and shown in FIGS. 4*a,b*. The reagent is deposited as a wet reagent droplet having substantially uniform structural parameters (CA, height h, radius R, and contact angle θ) from test sensor to test sensor. It is contemplated that base, the lid and/or the spacer are attached before the wet reagent droplet dries.

According to another method, an electrochemical test sensor is formed having a dry reagent layer. The method includes providing a base or substrate, forming an electrode pattern on the base, depositing a wet reagent droplet on at least the electrode pattern, drying the wet reagent droplet to form the dry reagent layer, providing a lid, and attaching the lid to the base. The reagent is deposited on the base and/or electrode pattern using a reagent-dispensing system 500 shown in FIG. 5*a*.

Figure 5B:
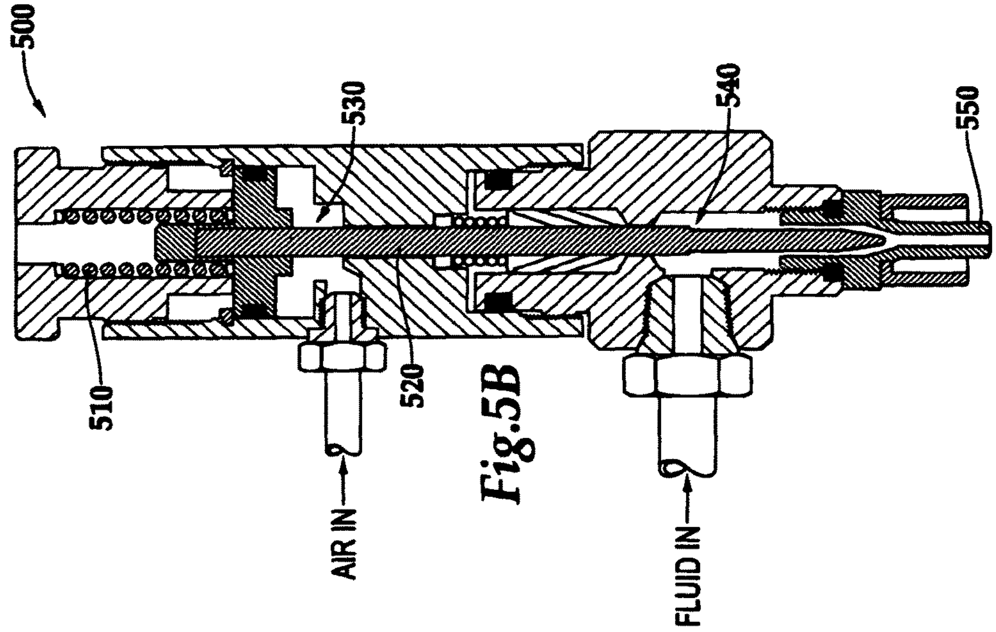
FIG. 5*b* depicts the piston-needle assembly and nozzle of FIG. 5*a* in the open position.
Figure 5A:
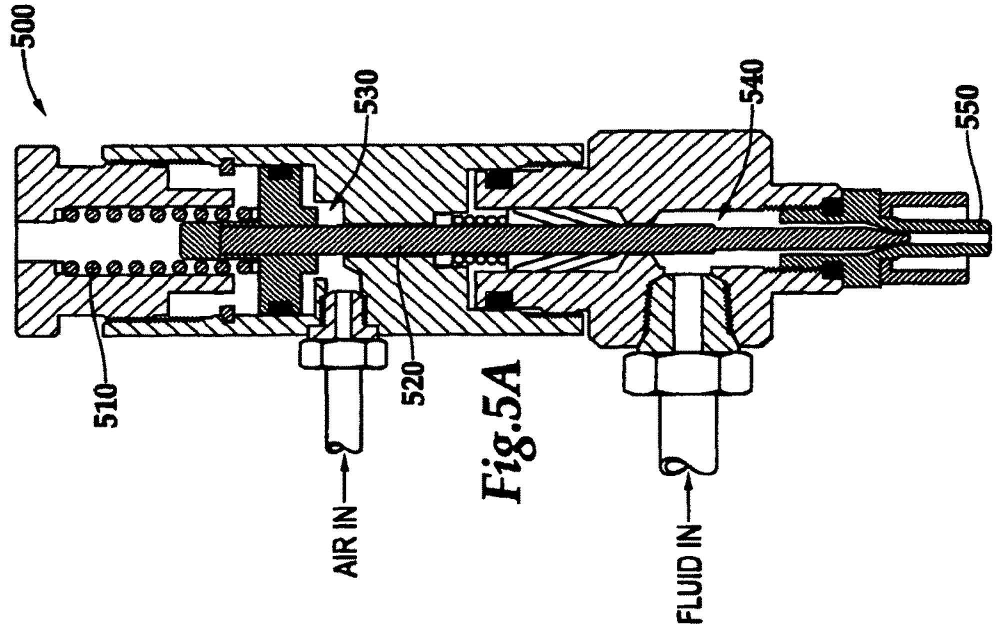
FIG. 5*a* is a cross-sectional side view of another reagent-dispensing system.

The reagent-dispensing system 500 includes a compression member 510, a piston-needle assembly 520, an air chamber 530, a fluid chamber 540, and a nozzle 550, which are similar to the compression member 410, the piston-needle assembly 420, the air chamber 430, the fluid chamber 440, and the nozzle 450 respectively, all described above and shown in FIGS. 4*a,b*. The reagent-dispensing system 500 has an open position and a closed position. FIG. 5*a* depicts the reagent-dispensing system 500 in the closed position; while FIG. 5*b* depicts the reagent-dispensing system 500 in the open position. The piston-needle assembly 520 oscillates between the open and closed positions, compressing the compression member 510, and forcing a portion of the reagent out of the nozzle 550. The portion of reagent is deposited on the base and/or electrode pattern as a wet reagent droplet having substantially uniform structural parameters (height h, radius R, and contact angle θ) from test sensor to test sensor.

Figure 6A:
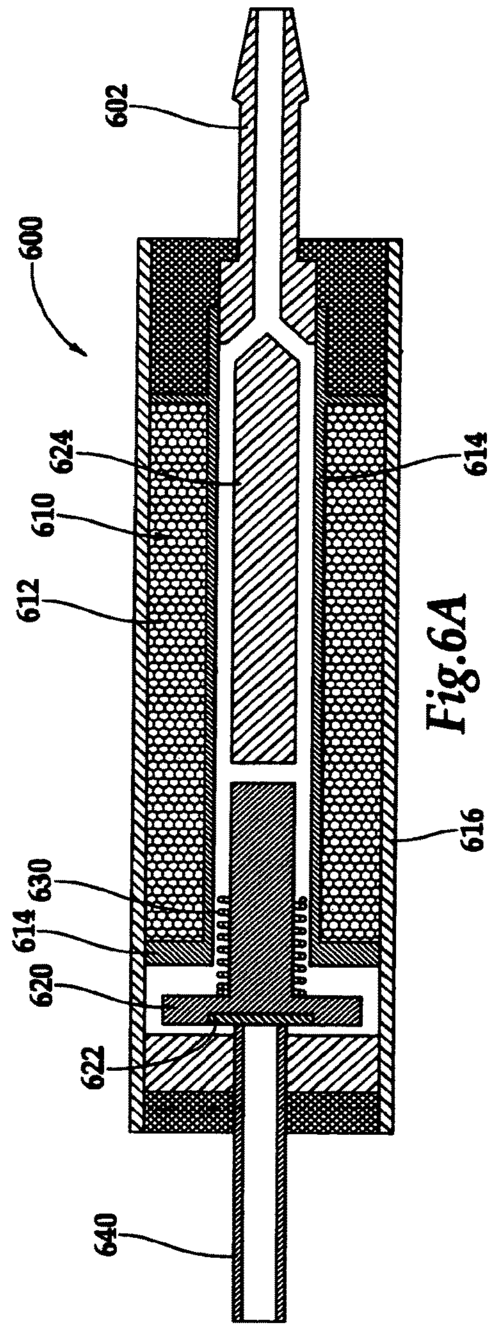
FIG. 6*a* is a cross-sectional side view of a reagent-dispensing system according to another method of the present invention.

According to another method, an electrochemical test sensor is formed having a dry reagent layer. The test sensor may be the same or similar to the test sensors 100, 200, 300 or 301 described above. The method includes providing a base or substrate and forming an electrode pattern on the base. The base and the electrode pattern may be the same or similar to the base 112 and the electrode pattern 130 described above and shown in FIG. 1*c*. A reagent-dispensing system is supplied for depositing reagent. It is contemplated that the reagent-dispensing system may deposit the reagent on the base, on the electrode pattern, or on a combination thereof. FIGS. 6*a,b* depict a cross-sectional side view of another non-limiting example of a reagent-dispensing system 600.

Figure 6B:
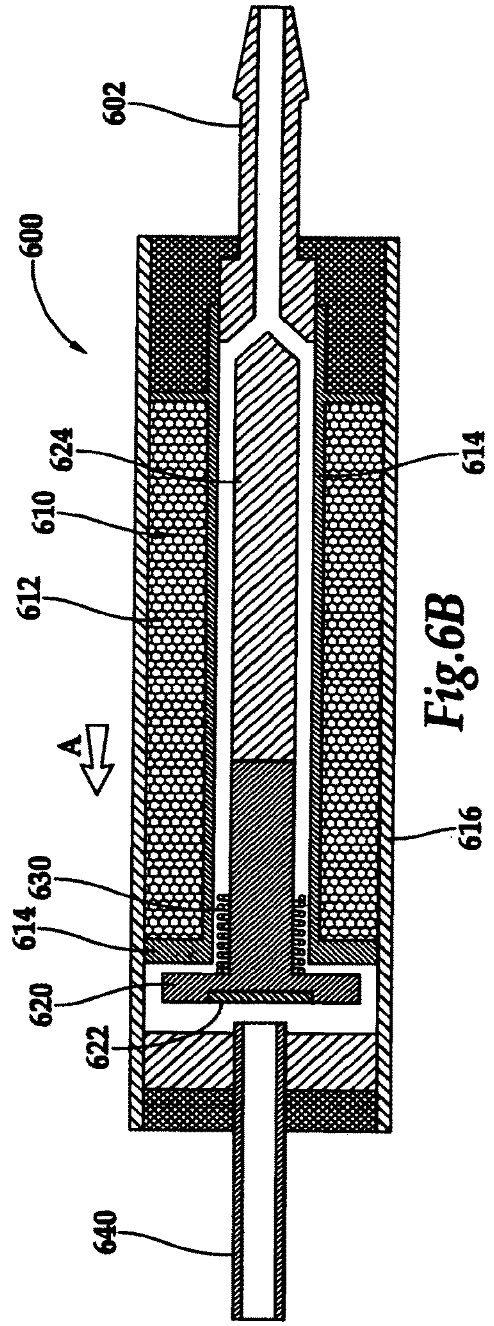
FIG. 6*b* depicts the reagent-dispensing system of FIG. 6*a* in the open position.

The reagent-dispensing system 600 includes a solenoid control valve 610, a plunger 620, a compression member 630, and a nozzle 640. The solenoid control valve 610 may be selectively opened and closed. An electrical signal may be supplied that triggers the solenoid control valve 610 to open. When the electrical signal is terminated, the solenoid control valve 610 closes. FIG. 6*a* depicts the solenoid control valve 610 in an open position, while FIG. 6*b* depicts the solenoid control valve 610 in a closed position. The solenoid control valve 610 comprises a coil 612, a bobbin 614, and a shield 616. It is contemplated that the sizes, shapes, and material of the coil 612, the bobbin 614, and the shield 616 may be different from those depicted in FIGS. 6*a,b*.

The plunger 620 is located in the general center of the solenoid control valve 610. The plunger has an open position and a closed position corresponding to the solenoid control valve 610 position. The plunger 620 also has two opposing ends. The first opposing end contains an integrated seal member 622 adapted to mate with the nozzle 640. The seal member 622 prevents or inhibits the reagent in the reagent-dispensing system 600 from exiting the nozzle 640 when the plunger 620 is in the closed position. The second opposing end of the plunger 620 is adapted to mate with a plunger stop 624. The plunger stop 624 is also located in the center of the solenoid control valve 610 and provides a surface for the second opposing end of the plunger 620 to abut when the solenoid control valve 610 is in the open position.

The compression member 630 biases the plunger 620 in the closed position. When the electrical signal triggers the solenoid control valve 610 to open, the plunger 620 is forced to compress the compression member 630. When the electrical signal terminates, the solenoid control valve 610 closes, allowing the compression member to slam or force the plunger 620 back into the closed position. It is contemplated that the compression member 630 may be, for example, but not limited to, a spring.

The nozzle 640 has an output diameter. It is contemplated that the output diameter of the nozzle 640 is generally of from about 4 to about 9 mils. It is desirable to have the nozzle 640 with an output diameter of from about 5 to about 8 mils, or more specifically, of from about 7 to about 8 mils. It is generally desirable to avoid smaller output diameters that correspond to an increased velocity of the reagent being deposited on the base and/or the electrode pattern resulting in splashing of the reagent. Additionally, a smaller output diameter nozzle requires a longer solenoid control valve open time to dispense a sufficient amount of the reagent onto the base and/or electrode pattern. It is also generally desirable to avoid larger output diameter nozzles that correspond to a very short solenoid control valve open time when the control valve is difficult to close for the needed amount of reagent.

Pressurized reagent is supplied to the reagent-dispensing system 600 through a fluid input 602. The electrical signal triggers the solenoid control valve 610 to open. The reagent is then forced through the solenoid control valve 610 and dispensed (in the direction of arrow A in FIG. 6*b*) onto the base and/or electrode pattern as a wet reagent droplet having substantially uniform parameters (h, R, and θ) from test sensor to test sensor. The pressure on the reagent adds kinetic energy to the reagent that makes the reagent less sensitive to surface variations, which produces the wet reagent droplet having uniform parameters.

It is contemplated that the reagent-dispensing system 600 may be located above the base and/or electrode pattern surface such that the reagent exiting the nozzle 640 increases in kinetic energy as the reagent is being deposited on the surface. This added kinetic energy further works to overcome contamination and surface variations of the base and/or electrode pattern to produce the wet reagent droplet with substantially uniform parameters from test sensor to test sensor.

The nozzle in one embodiment is generally located at a dispensing height of from about 50 to about 600 mils above the top surface of the base and/or electrode pattern. For more hydrophobic deposition surfaces having a contact angle θ from about 50 to about 100 degrees, it is desirable to have a dispensing height of from about 375 to about 425 mils. For more hydrophilic deposition surfaces having a contact angle θ from about 20 to about 50 degrees, it is desirable to have a dispensing height of from about 200 to about 250 mils. Some non-limiting examples of more hydrophilic surfaces include, but are not limited to, plasma-treated surfaces, wetted surfaces, and polished surfaces. It is also contemplated that the amount of fluid pressure on the reagent is from about 1 to about 20 psi. It is desirable for the fluid pressure to be from about 6 to about 9 psi for both hydrophobic and hydrophilic surfaces.

According to another method, an electrochemical test sensor is formed having a dry reagent layer. The test sensor may be the same or similar to the test sensors 100, 200, 300 or 301 described above. The method includes providing a base or substrate, forming an electrode pattern on the base, depositing a wet reagent droplet on at least the electrode pattern, drying the wet reagent droplet to form the dry reagent layer, providing a lid, and attaching the lid to the base. It is contemplated that a spacer may be provided similar to the spacer 114 described above in relation to the test sensor 100. The base, the electrode pattern, and the lid may be the same or similar to the base 112, the electrode pattern 130, and the lid 116 described above and shown in FIG. 1*a*. It is contemplated that the reagent is deposited on the base, the electrode pattern, or a combination thereof. The reagent is deposited on the base and/or electrode pattern using the same or similar reagent-dispensing system as the reagent-dispensing system 600 described above and shown in FIGS. 6*a,b*. The reagent is deposited on the base and/or electrode pattern as a wet reagent droplet having one or more structural parameters including covering area CA, height h, radius R, and contact angle θ. It is contemplated that the base, the lid and/or the spacer are attached before the wet reagent droplet dries.

In one method, the electrochemical test sensors, 100, 200, 300 or 301 described above, may be formed from ribbon strips. The ribbon strips may be made from processes such as a multiple-sheet process or a web process. For example, in an embodiment with a base, a spacer, and lid, a base-ribbon strip, a spacer-ribbon strip, and a lid-ribbon strip may be used. For improved efficiency, the electrochemical test sensors are generally formed after all of the ribbon strips have been attached. In another embodiment, the base-ribbon strip is adapted to be attached (e.g., laminated) with a second layer such as, for example, a lid-ribbon strip.

Figure 7:
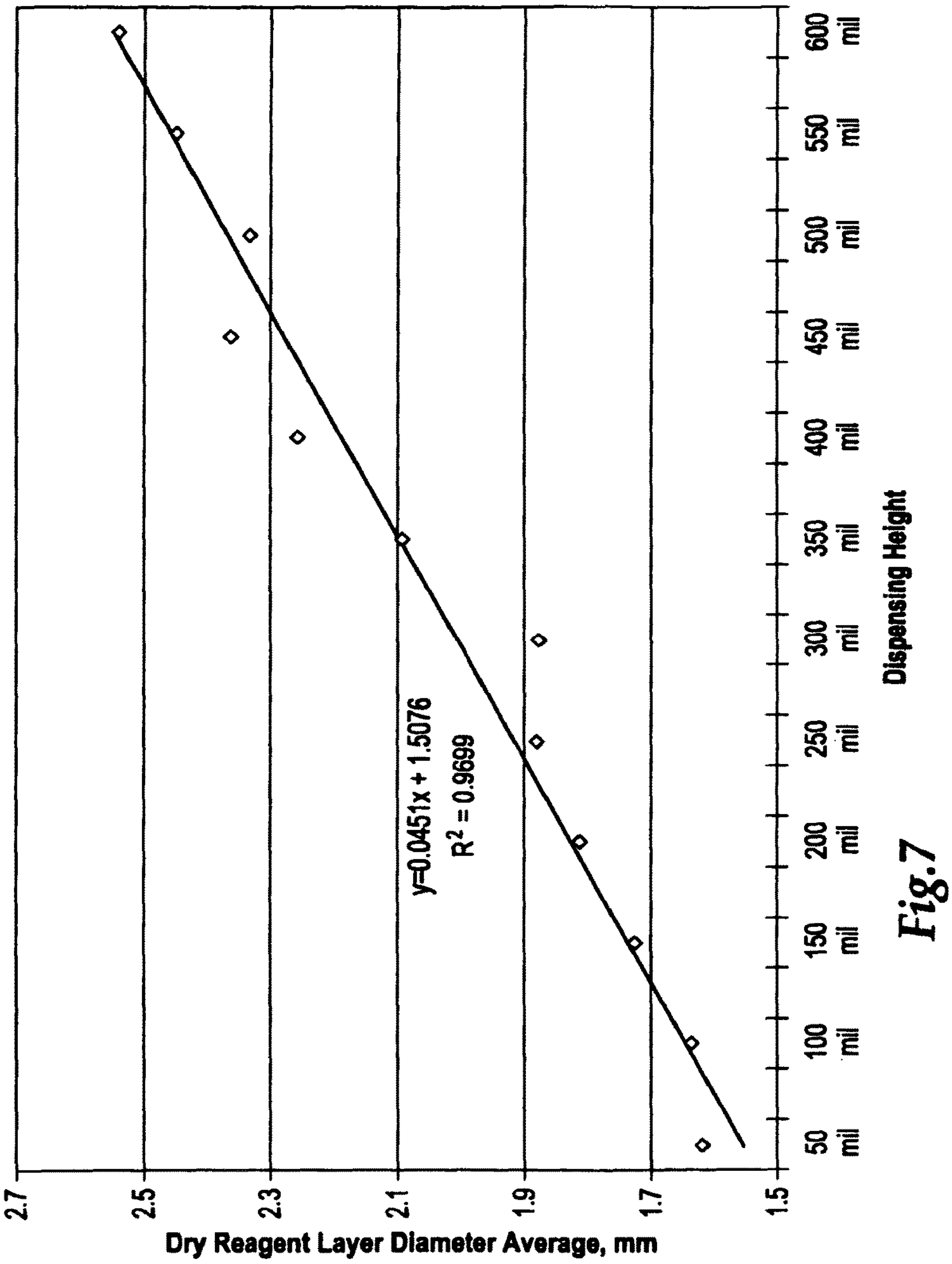
FIG. 7 graphically depicts the linear correlation between the diameters of dry reagent layers to the dispensing height of the reagent-dispensing system shown in FIGS. 6*a,b*.

Referring to FIG. 7, a chart is shown depicting the correlation between the dry reagent layer's diameter and the dispensing height of the reagent-dispensing system 600. Specifically, a linear relationship exists between the dispensing height and the diameter of the dry reagent layer. As the dispensing height increases, the diameter of the dry reagent layer also increases.

In another method, the test sensors may be optical test sensors. Optical test sensor systems may use techniques such as, for example, transmission spectroscopy, diffuse reflectance, or fluorescence spectroscopy for measuring information relating to the fluid analyte such as, for example, the analyte concentration. An indicator reagent system and an analyte in a sample of body fluid are reacted to produce a chromatic reaction, as the reaction between the reagent and analyte causes, the sample to change color. The degree of color change is indicative of the analyte concentration in the body fluid. The color change of the sample is evaluated to measure the absorbance level of the transmitted light.

One non-limiting example of an optical test sensor 800 is depicted in FIGS. 8*a,b*. The optical test sensor 800 includes a base 812, a spacer 814, a lid 816, and a testing portion 850. The base 812, the spacer 814, and the lid 816 may be similar or the same as the base, the spacer, and the lid disclosed in test sensors 100, 200, 300 and 301. Alternatively, the optical test sensor may include a base, a lid, and a testing portion 850. The optical test sensor, however, would not need to include electrodes, conductive leads, or test-sensor contacts disclosed in the electrochemical test sensors. To form the test sensor 800, the base 812, the spacer 814, and the lid 816 are attached by, for example, an adhesive or heat sealing. A channel 820 (e.g., capillary channel) is formed when the base 812, the spacer 814, and the lid 816 are attached to each other. The lid 816 may include a vent 817 to assist the flow of the fluid sample into the channel 820. The testing portion 850 includes a dry reagent layer 852. The dry reagent layer 852 may be formed by dispensing a wet reagent droplet on the base 812 using the reagent-dispensing systems 400 or 600 described above and shown in FIGS. 4*a,b* and 6*a,b* respectively.

Any of the above described reagent-dispensing systems (400, 500, and 600) can deposit reagent as wet reagent droplets having a substantially uniform covering area between about one square millimeter to about twenty square millimeters from test sensor to test sensor. It is contemplated that according to some embodiments, each of the wet reagent droplets have a substantially uniform covering area of about three square millimeters to about six square millimeters. Any of the above described reagent-dispensing systems can also deposit reagent as wet reagent droplets having a substantially uniform height h of about ten micrometers to about three hundred micrometers. It is contemplated that according to some embodiments, the wet reagent droplets have a substantially uniform height h of about forty micrometers to about one hundred micrometers.

Each of the wet reagent droplets dry into a respective dry reagent layers having substantially the same covering area as the wet reagent droplets. The dry reagent layers have a substantially uniform height h of about one-half of a micrometer to about twenty micrometers. It is contemplated that according to some embodiments, the dry reagent layers have a substantially uniform height h of about one micrometer to about five micrometers.

In addition to the depositing techniques described above, the reagent uniformity may be improved by the reagent formulation itself. As discussed above, the dry reagent layer 152 converts an analyte of interest (e.g., glucose) in the fluid sample (e.g., blood) into a chemical species that is electrochemically measurable, in terms of the electrical current it produces, by the components of the electrode pattern 130. The reagent typically includes an enzyme and a mediator. An appropriately enzyme is selected to react with the desired analyte or analytes to be tested. An enzyme that may be used to react with glucose is glucose oxidase. It is contemplated that other enzymes may be used to react with glucose such as glucose dehydrogenase. It is contemplated that other enzymes may be used to react with another analytes.

The reagent typically includes a mediator that assists in transferring electrons between the analyte and the electrodes. Mediators that may be used include, but are not limited to, ferricyanide, phenazine ethosulphate, phenazine methosulfate, phenylenediamine, 1-methoxy-phenazine methosulfate, 2,6-dimethyl-1,4-benzoquinone, 2,5-dichloro-1,4-benzoquinone, ferrocene derivatives; osmium bipyridyl complexes, ruthenium complexes, 3-phenylimino-3H-phenothiazines, 3-phenylimino-3H-phenoxazines and the like. In those embodiments, where glucose is the analyte of interest and glucose oxidase or glucose dehydrogenase is the enzyme components, a mediator of particular interest is ferricyanide.

The reagent may include binders that hold the enzyme and mediator together, other inert ingredients, buffers or combinations thereof. Other components that may be present in the reagent include buffering agents (e.g., citraconate, citrate, malic, maleic and phosphate) and binders (e.g., cellulose polymers). Other components that may be present in the reagent include co-enzymes such as pyrroloquinoline quinine (PQQ), flavin adenine dinucleotide (FAD) and nicotinamide adenine dinucleotide (phosphate) (NAD(P)), surfactants such as Triton®, Macol®, Tetronic®, Silwet®, Zonyl®, and Pluronic®, and stabilizing agents such as albumin, sucrose, trehalose, mannitol, and lactose.

When a spilled drop of coffee dries on a solid surface, it leaves a dense, ring-like stain along the perimeter. The coffee, initially dispersed over the entire drop, becomes concentrated into a tiny fraction of it. This phenomenon is referred to as "coffee ring" effect. Physically, the coffee ring is formed because any liquid that evaporates from the edge must be replenished by liquid from the interior. As this process ends, more materials are accumulated onto the edge. When an electrochemical test sensor is formed, a chemical reagent including an enzyme and mediator is applied to and dried on an electrode surface. The chemical reagent may be applied by methods such as screen printing, strip coating and micro-deposition. During micro-deposition, the reagent is relatively thin and has a viscosity less than about 1,000 centipoise (cp) and desirably is less than about 100 cp. This relatively thin reagent may produce the coffee ring effect described above.

To improve the reagent uniformity onto the base of the test sensor, the formulation of the reagent may be optimized by including a concentrated multivalent salt and/or a polyelectrolyte. The use of a concentrated multivalent salt and/or a polyelectrolyte in the reagent may reduce or even eliminate the coffee ring effect.

The multivalent salts typically have a concentration of at least 40 mM in the reagent solution and more desirably have a concentration of at least 50 mM in the reagent solution. To further improve the uniformity of the reagent, the multivalent salts may have a higher concentration of at least 60 or 75 mM in the reagent solution and or even a concentration of at least 100 mM in the reagent solution. The multivalent salts to be used should have sufficient solubility at room temperature in the reagent solution to reach a desired concentration.

Non-limiting examples of multivalent salts include sulfates and phosphates such as sodium sulfate ($Na_2SO_4$), potassium sulfate ($K_2SO_4$), ammonium sulfate ($(NH_4)_2SO_4$), dibasic sodium phosphate ($Na_2HPO_4$), dibasic potassium phosphate ($K_2HPO_4$), dibasic ammonium phosphate ($(NH_4)_2HPO_4$), sodium oxalate ($Na_2C_2O_4$), potassium oxalate ($K_2C_2O_4$), sodium succinate ($Na_2C_4H_4O_4$) and potassium succinate ($K_2C_4H_4O_4$). The selected multivalent salts, including sulfates and phosphates, have desirable water solubilities to assist in improving reagent uniformity.

Some non-limiting examples of polyelectrolytes that may be used include, but are not limited to, carboxymethyl cellulose (CMC), homopolymer and copolymers of arylic acid, malaic acid, styrenesulfonic acid, vinylsulfonic acid, copolymers or salts thereof. One example of a polyelectrolyte is Gantrez® (a methylvinylether/maleic anhydride copolymer) from International Specialty Products. The weight percentage of the polyelectrolytes in the reagent may vary but are generally from about 0.1 to about 4 wt. % and, more specifically, from about 0.2 to about 1 wt. % of the reagent. The polyelectrolytes are generally at least about 0.2 or at least about 0.3 wt. % of the reagent. The amount of polyelectrolytes should be much selected such that filtration and volume precision are not affected.

In addition to concentrated multivalent salts and polyelectrolytes, reagent solid loading may be increased from about 5 to about 15 wt. % without significant impact on reagent viscosity by selecting low molecular weight polymers as a binder. With the kinetic dispense force described above, the wet reagent can be dispensed to have an average thickness of 100 μm and, more desirably, 50 μm or less. Thin wet reagent requires shorter times to dry, and greatly reduces the component accumulation towards the edge.

EXAMPLES

Example 1

FIG. 9 shows a plot of height (in μm) versus distance (in mm) of a cross-sectional view taken generally across a dried reagent drop on the substrate. The dried reagent included 2 units/μL of flavin adenine dinucleotide-glucose dehydrogenase (FAD-GDH) enzyme, 60 mM of 3-(2',5'-disulfophenylimino)-3H-phenothiazine mediator, 0.15 wt. % Mega 8 surfactant, 0.38 wt. % hydroxyethyl cellulose, 12 mM sodium sulfate, and 40 mM of $Na_2HPO_4$ in phosphate buffer (total phosphate buffer concentration of 125 mM) having a pH of about 6.5. Thus, the concentration of multivalent salt was over 52 mM.

The reagent was dispensed with INKA Series miniature solenoid valves from Lee Company of Westbrook, Conn. The reagent was dried using a Lindberg tunneled oven. To assist in providing data for the plot of FIG. 9, a MicroProf®

MPR140 (Fries Research & Technology GmbH, Bergisch-Glabach, Germany) assisted in characterizing the reagent 3-D structure.

As shown in FIG. 9, the height at the extreme ends reflects the baseline height of the substrate itself since the width of the substrate is greater than the width of the dried reagent drop. The height was roughly consistent across the dried reagent drop but there were a few outliers. The roughly consistent height indicates that the concentration of the solids was more uniform across the width of the dried reagent drop. The uniformity may be defined as the ratio of the thinnest point to the thickest point (i.e., the ratio of the thinnest point in the plot of the height to the thickest point in the height). For example in FIG. 10, the ratio was about 1.2/5.5 or 0.22. This ratio was lower because of the outliers. The middle section of the graph (from about 0.5 to about 2.0 distance in FIG. 9 or roughly the middle 60%) averaged about 2.75 in height. The ratio of the average middle section to the thickest point was a much better 0.5.

It is desirable for the ratio of the thinnest point to the thickest point in the dried reagent drop to be greater than about 0.2. It is even more desirable for the ratio of the thinnest point to the thickest point in the dried reagent drop to be greater than about 0.3 or 0.4. It is even more desirable for the ratio of the thinnest point to the thickest point in the dried reagent drop to be greater than about 0.5 or 0.6.

It is desirable for the ratio of the average middle section to the thickest point in the dried reagent drop to be greater than about 0.4. It is even more desirable for the average middle section to the thickest point in the dried reagent drop to be greater than about 0.5 or 0.6.

Example 2

Figure 10:
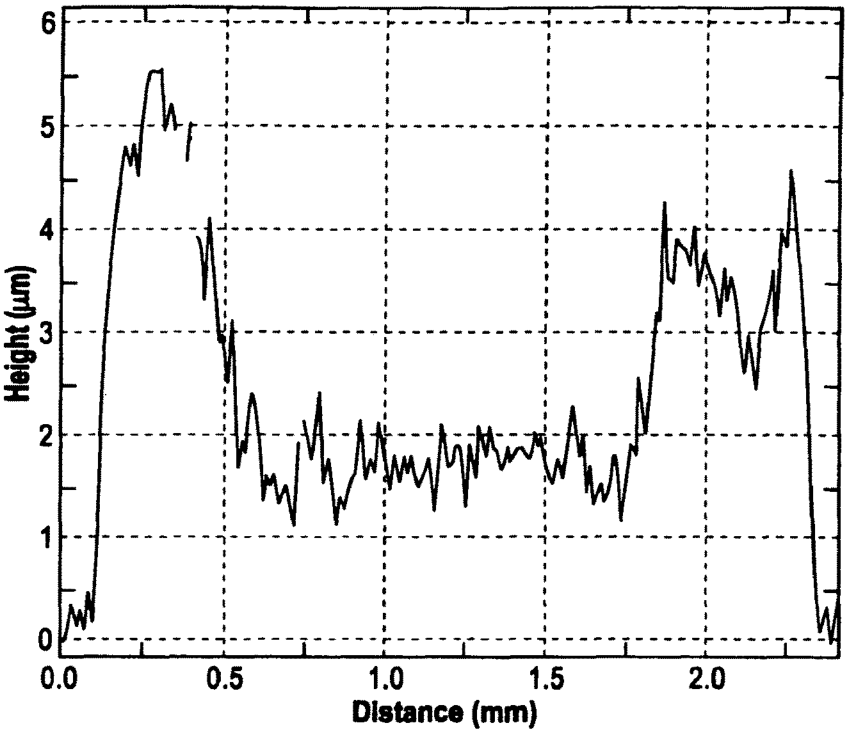

FIG. 10 shows a plot of height (in μm) versus distance (in mm) of a cross-sectional view taken generally across a dried reagent drop on the substrate. The dried reagent included 2 units/μL of FAD-GDH enzyme, 60 mM of 3-(2',5'-disulfophenylimino)-3H-phenothiazine mediator, 0.15 wt. % Mega 8 surfactant, 0.38 wt. % hydroxyethyl cellulose, 12 mM sodium sulfate, and 24 mM of $Na_2HPO_4$ in phosphate buffer (total phosphate buffer concentration of 75 mM) having a pH of about 6.5. Thus, the concentration of multivalent salt was over 38 mM.

As shown in FIG. 10, the height at the extreme ends reflects the baseline height of the substrate itself since the width of the substrate is greater than the width of the dried reagent drop. The height was much less consistent than depicted above in FIG. 9. The height was higher at the ends of the dried reagent drop as compared to FIG. 9, which indicates less uniformity in the dried reagent drop of FIG. 10 as compared to the dried reagent drop of FIG. 9. In FIG. 10, the ratio of the thinnest point to the thickest point was about 1.1/5.5 or 0.20. The middle section of the graph (from about 0.5 to about 2.0 distance in FIG. 9 or roughly the middle 60%) averaged about 1.75 in height. The ratio of the average middle section to the thickest point was 0.32. Thus, although the ratio of the thinnest point to the thickest point in FIG. 10 was about the same as FIG. 9, the average middle section was much thinner than in the average middle section of FIG. 9, resulting in a less uniform structure.

Example 3

Figure 11:
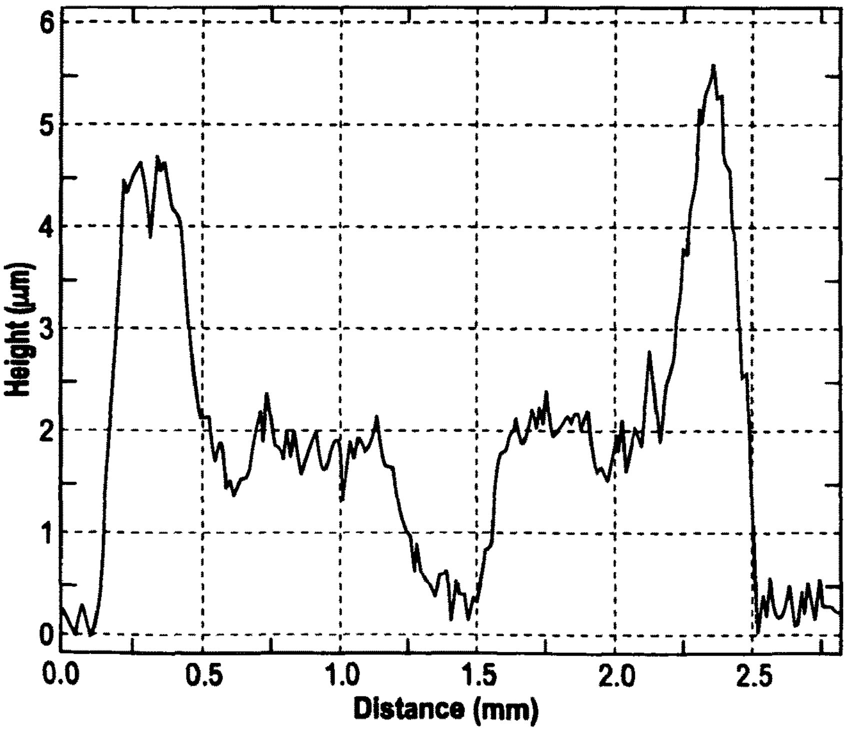

FIG. 11 shows a plot of height (in μm) versus distance (in mm) of a cross-sectional view taken generally across a dried reagent drop on the substrate. The dried reagent included 2 units/μL of FAD-GDH enzyme, 40 mM of 3-(2',5'-disulfophenylimino)-3H-phenothiazine mediator, 0.2 wt. % Mega 8 surfactant, 0.25 wt. % hydroxyethyl cellulose, 5 mM sodium sulfate, and 16 mM of $Na_2HPO_4$ in phosphate buffer (total phosphate buffer concentration of 50 mM) having a pH of about 6.5. Thus, the concentration of multivalent salt was 21 mM in the reagent solution. The total volume of the reagent was 0.45 μL.

As shown in FIG. 11, the height at the extreme ends reflects the baseline height of the substrate itself since the width of the substrate is greater than the width of the dried reagent drop. The height was higher at the ends of the dried reagent drop, which indicates less uniformity in the dried reagent drop. More specifically, the dried reagent of FIG. 11 formed a hole in its center, while a thick ring was formed along its edges that contained solids.

For example in FIG. 11, the ratio of the thinnest point to the thickest point was about 0.2/5.5 or 0.04.

Example 4

Figure 12:
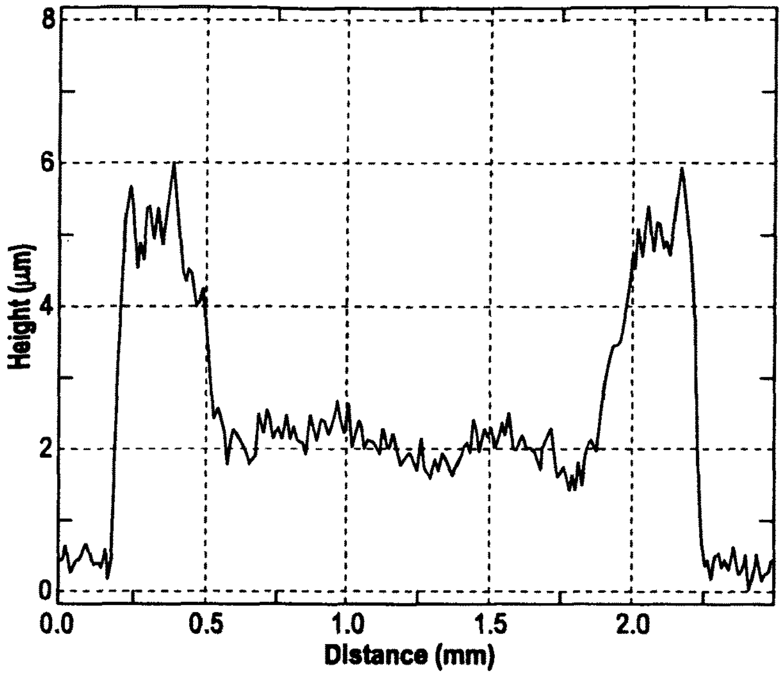

FIG. 12 shows a plot of height (in μm) versus distance (in mm) of a cross-sectional view taken generally across a dried reagent drop on the substrate. The dried reagent included 3 units/μL of FAD-GDH enzyme, 60 mM of 3-(2',5'-disulfophenylimino)-3H-phenothiazine mediator, 0.3 wt. % Mega 8 surfactant, 0.375 wt. % hydroxyethyl cellulose, 7.5 mM sodium sulfate, and 24 mM of $Na_2HPO_4$ in phosphate buffer (total phosphate buffer concentration of 75 mM) having a pH of about 6.5. Thus, the concentration of multivalent salt was 31.5 mM in the reagent solution. The total volume of the reagent was 0.30 μL.

As shown in FIG. 12, the height at the extreme ends reflects the baseline height of the substrate itself since the width of the substrate is greater than the width of the dried reagent drop. The consistency of the height was much better than that of FIG. 11 (Example 3), but was less consistent than depicted below in FIG. 13 (Example 5). The solids were not as concentrated towards the ends as shown in FIG. 11, which indicated more uniformity in the dried reagent drop.

For example in FIG. 11, the ratio was about 1.7/6.0 or 0.28. The middle section of the graph (from about 0.5 to about 2.0 distance in FIG. 9 or roughly the middle 60%) averaged about 2.0 in height. The ratio of the average middle section to the thickest point was 0.33.

Example 5

Figure 13:
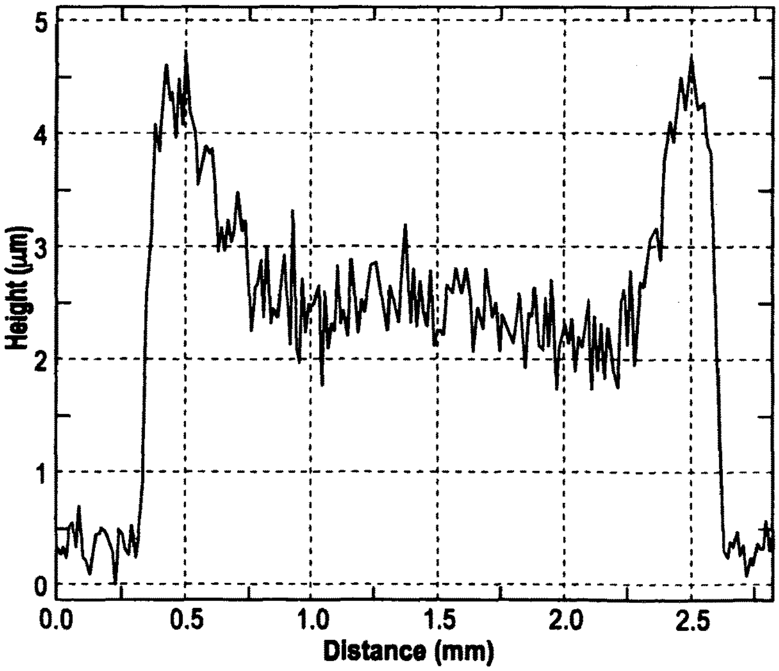

FIG. 13 shows a plot of height (in μm) versus distance (in mm) of a cross-sectional view taken generally across a dried reagent drop on the substrate. The dried reagent included 4.5 units/μL of FAD-GDH enzyme, 90 mM of 3-(2',5'-disulfophenylimino)-3H-phenothiazine mediator, 0.45 wt. % Mega 8 surfactant, 0.56 wt. % hydroxyethyl cellulose, 11.2 mM sodium sulfate, and 36 mM of $Na_2HPO_4$ in phosphate buffer (total phosphate buffer concentration of 112 mM) having a pH of about 6.5. Thus, the concentration of multivalent salt was over 47 mM in the reagent solution. The total volume of the reagent was 0.20 μL.

For example in FIG. 13, the ratio was about 1.7/4.5 or 0.38. The middle section of the graph (from about 0.5 to about 2.0 distance in FIG. 9 or roughly the middle 60%) averaged about 2.5 in height. The ratio of the average middle section to the thickest point was 0.55.

As shown in FIG. 13, the height at the extreme ends reflects the baseline height of the substrate itself since the width of the substrate is greater than the width of the dried reagent drop. The consistency of the height of the cross-sectional view of the dried reagent drop was much better than that shown in FIGS. 11 and 12 (Examples 3 and 4, respectively). Thus, the dried reagent drop has more uniformity than shown in FIGS. 11 and 12.

Alternate Embodiment A

A method of depositing reagent on an electrochemical test sensor, the test sensor adapted to determine information relating to an analyte, the method comprising the acts of:

providing a base;

forming an electrode pattern on the base; and depositing the reagent on at least the electrode pattern using a reagent-dispensing system, the reagent-dispensing system applying mechanical force to the reagent in the reagent-dispensing system to assist in providing a wet reagent droplet on at least the electrode pattern.

Alternate Embodiment B

A method of forming an electrochemical test sensor, the test sensor being adapted to determine information relating to an analyte, the method comprising the acts of:

providing a base;

forming an electrode pattern on the base;

providing a reagent-dispensing system for depositing reagent on at least the electrode pattern, the reagent-dispensing system including a compression member, a piston-needle assembly, an air chamber, a fluid chamber, a nozzle, and a body, the compression member having a compression-adjustment mechanism for adjusting the amount of compression, the piston-needle assembly having a closed position and an open position;

supplying the reagent into the fluid chamber, the fluid chamber having a fluid input and a fluid output, the fluid output having an open position and a closed position corresponding to the open and closed positions of the piston-needle assembly;

supplying pressurized air to the air chamber to cause the piston-needle assembly to compress the compression member, the piston-needle assembly being in the open position, the fluid output being in the open position; and releasing the supplied pressurized air from the air chamber to allow the compression member to force the piston-needle assembly into the closed position, the piston-needle assembly mechanically forcing a portion of the reagent in the fluid chamber out of the nozzle, the portion of the reagent being deposited on at least the electrode pattern as a wet reagent droplet.

Alternate Embodiment C

The method of alternate embodiment B, further comprising the acts of:

providing a lid; and attaching the lid to the base to assist in forming a channel in the test sensor, the channel assisting in allowing a fluid sample to contact the reagent droplet deposited on at least the electrode pattern.

Alternate Embodiment D

The method of alternate embodiment B, further comprising the acts of:

providing a spacer;

providing a lid; and attaching the lid to the spacer and attaching the spacer to the base to assist in forming a channel in the test sensor, the channel assisting in allowing a fluid sample to contact the reagent droplet deposited on at least the electrode pattern.

Alternate Embodiment E

The method of alternate embodiment B, further comprising the act of providing a solenoid valve to assist in supplying the pressurized air to the air chamber and to assist in releasing the supplied pressurized air from the air chamber.

Alternate Embodiment F

The method of alternate embodiment B, wherein the solenoid valve is selectively opened or closed by an electrical trigger.

Alternate Embodiment G

The method of alternate embodiment B, further comprising the acts of:

drying the wet reagent droplet to form a dry reagent layer;

providing a lid; and attaching the lid to the base to assist in forming a channel in the test sensor, the channel assisting in allowing a fluid sample to contact the dry reagent layer on at least the electrode pattern.

Alternate Embodiment H

A method of forming an electrochemical test sensor, the test sensor being adapted to determine information relating to an analyte, the method comprising the acts of:

providing a base;

forming an electrode pattern on the base;

providing a reagent-dispensing system for depositing reagent on at least the electrode pattern, the reagent-dispensing system including a solenoid control valve, a plunger, a compression member, and a nozzle, the nozzle having an output diameter, the solenoid control valve having an open position and a closed position;

supplying pressurized reagent; and opening the control valve of the reagent-dispensing system to cause the pressurized reagent to be dispensed through the nozzle and deposited on at least the electrode pattern as a wet reagent droplet.

Alternate Embodiment I

The method of alternate embodiment H, wherein the nozzle output diameter is from about 3.5 mils to about 9.5 mils.

Alternate Embodiment J

The method of alternate embodiment H, further comprising the acts of locating the nozzle of the reagent-dispensing system at a dispensing height of from about 50 mils to about 600 mils above a top surface of the electrode pattern.

Alternate Embodiment K

The method of alternate embodiment J, further comprising the acts of locating the nozzle of the reagent-dispensing system at a dispensing height of from about 375 mils to about 425 mils.

Alternate Embodiment L

The method of alternate embodiment J, further comprising the acts of locating the nozzle of the reagent-dispensing system at a dispensing height of from about 200 mils to about 250 mils, wherein the electrode pattern is plasma treated.

Alternate Embodiment M

The method of alternate embodiment H, further comprising the acts of;

providing a lid; and attaching the lid to the base to assist in forming a channel in the test sensor, the channel assisting in allowing a fluid sample to contact the reagent droplet located on at least the electrode pattern.

Alternate Embodiment N

The method of alternate embodiment H, further comprising the acts of;

providing a spacer;

providing a lid; and attaching the lid to the spacer and attaching the spacer to the base to assist in forming a channel in the test sensor, the channel assisting in allowing a fluid sample to contact the reagent droplet located on at least the electrode pattern.

Alternate Embodiment O

The method of alternate embodiment H, further comprising the acts of;

drying the wet reagent droplet to form a dry reagent layer;

providing a lid; and attaching the lid to the base to assist in forming a channel in the test sensor, the channel assisting in allowing a fluid sample to contact the dry reagent layer located on at least the electrode pattern.

Alternate Embodiment P

A method of forming an optical test sensor, the optical test sensor being adapted to determine information relating to an analyte, the method comprising the acts of:

providing a base;

providing a reagent-dispensing system for depositing reagent on the base, the reagent-dispensing system including a solenoid control valve, a plunger, a compression member, and a nozzle, the nozzle having an output diameter, the solenoid control valve having an open and a closed position;

supplying pressurized reagent;

opening the control valve of the reagent-dispensing system to cause the supplied pressurized reagent to be dispensed through the nozzle and deposited on the base as a wet reagent droplet;

drying the wet reagent droplet to form a dry reagent layer;

providing a lid; and attaching the lid to the base to assist in forming a channel in the test sensor, the channel assisting in allowing a fluid sample to contact the dry reagent layer located on the base.

Alternate Embodiment Q

An electrochemical test sensor comprising a base, a lid, a plurality of electrodes and a dried reagent, the dried reagent including an enzyme, a mediator, and a sufficient amount of a multivalent salt such that dried reagent has a uniformity in which the ratio of the thinnest point to the thickest point is greater than about 0.2.

Alternate Embodiment R

The electrochemical test sensor of embodiment Q wherein the dried reagent has a uniformity in which the ratio of the thinnest point to the thickest point is greater than about 0.3.

Alternate Embodiment S

The electrochemical test sensor of embodiment R wherein the dried reagent has a uniformity in which the ratio of the thinnest point to the thickest point is greater than about 0.4.

Alternate Embodiment T

A method of forming an electrochemical test sensor, the method comprising:

providing a base and a lid, forming a plurality of electrodes on at least one of the base and the lid;

placing reagent solution so as to be in contact with at least one of the electrodes, the reagent solution including an enzyme, a mediator, and a multivalent salt, the multivalent salt having a concentration greater than 40 mM in the reagent solution; and drying the reagent solution after placement thereof.

Alternate Embodiment U

The method of process T wherein the multivalent salt is sodium sulfate ($Na_2SO_4$), potassium sulfate ($K_2SO_4$), ammonium sulfate ($(NH_4)_2SO_4$), dibasic sodium phosphate ($Na_2HPO_4$), dibasic potassium phosphate ($K_2HPO_4$), dibasic ammonium phosphate $(NH_4)_2HPO_4$), sodium oxalate ($Na_2C_2O_4$), potassium oxalate ($K_2C_2O_4$), sodium succinate ($Na_2C_4H_4O_4$), potassium succinate ($K_2C_4H_4O_4$) or a combination thereof.

Alternate Embodiment V

The method of process T wherein the multivalent salt is a sulfate, a phosphate or a combination thereof.

Alternate Embodiment W

The method of process T wherein the multivalent salt has a concentration greater than 50 mM in the reagent solution.

Alternate Embodiment X

The method of process W wherein the multivalent salt has a concentration greater than 75 mM in the reagent solution.

Alternate Embodiment Y

The method of process T wherein the dried reagent has a uniformity in which the ratio of the thinnest point to the thickest point is greater than 0.3.

Alternate Embodiment Z

A method of forming an electrochemical test sensor, the method comprising:

providing a base and a lid, forming a plurality of electrodes on at least one of the base and the lid;

placing a reagent solution so as to be in contact with at least one of the electrodes, the reagent solution including an enzyme, a mediator, and an electrolyte, the electrolyte being at least 0.1 wt. % of the reagent solution; and drying the reagent solution after placement thereof.

Alternate Embodiment AA

The method of process Z wherein the polyelectrolyte includes carboxymethyl cellulose (CMC), homopolymer and copolymers of arylic acid, malaic acid, styrenesulfonic acid, vinylsulfonic acid, copolymers or salts thereof.

Alternate Embodiment BB

The method of process Z wherein the reagent solution includes at least about 0.2 wt. % polyelectrolytes.

Alternate Embodiment CC

The method of process BB wherein the reagent solution includes at least about 0.3 wt. % polyelectrolytes.

Alternate Embodiment DD

The method of process Z wherein the dried reagent has a uniformity in which the ratio of the thinnest point to the thickest point is greater than 0.2.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents, and alternatives falling within the spirit and scope of the invention.

What is claimed is:

1. A method of forming an electrochemical test sensor, the method comprising:

providing a base and a lid;

forming a plurality of electrodes on at least one of the base and the lid;

dropping a reagent solution droplet so as to be in contact with at least one of the electrodes, the reagent solution droplet including an enzyme, a mediator, and a polyelectrolyte, the reagent solution droplet including at least 0.1 wt. % of the polyelectrolyte; and drying the reagent solution droplet after placement thereof such that dried reagent has a uniformity in which the ratio of the thinnest point to the thickest point is greater than about 0.2, wherein the thickness of the dried reagent is from about 0.5 to about 20 micrometers (μm).

2. The method of claim 1, wherein the polyelectrolyte includes carboxymethyl cellulose (CMC), homopolymer and copolymers of arylic acid, malaic acid, styrenesulfonic acid, vinylsulfonic acid, copolymers or salts thereof.

3. The method of claim 1, wherein the reagent solution droplet includes at least about 0.3 wt. % polyelectrolytes.

4. The method of claim 3, wherein the reagent solution droplet includes at least about 0.4 wt. % polyelectrolytes.

5. The method of claim 1, wherein the dried reagent has a uniformity in which the ratio of the thinnest point to the thickest point is greater than 0.3.

6. The method of claim 1, wherein the thickness of the dried reagent is from about 1 to about 5 micrometers (μm).

7. The method of claim 1, wherein the thickness of the dried reagent is from about 0.5 to about 5 micrometers (μm).

8. A method of forming an electrochemical test sensor, the method comprising:

providing a base and a lid;

forming a plurality of electrodes on at least one of the base and the lid;

dropping a reagent solution droplet so as to be in contact with at least one of the electrodes, the reagent solution droplet including an enzyme, a mediator, and a multivalent salt, the multivalent salt having a concentration greater than 40 mM in the reagent solution droplet; and drying the reagent solution droplet after placement thereof such that dried reagent has a uniformity in which the ratio of the thinnest point to the thickest point is greater than about 0.2, wherein the thickness of the dried reagent is from about 0.5 to about 20 micrometers (μm).

9. The method of claim 8, wherein the multivalent salt is sodium sulfate (Na2SO4), potassium sulfate (K2SO4), ammonium sulfate ((NH4)2SO4), dibasic sodium phosphate (Na2HPO4), dibasic potassium phosphate (K2HPO4), dibasic ammonium phosphate (NH4)2HPO4), sodium oxalate (Na2C2O4), potassium oxalate (K2C2O4), sodium succinate (Na2C4H4O4), potassium succinate (K2C4H4O4), or a combination thereof.

10. The method of claim 8, wherein the multivalent salt has a concentration greater than 75 mM in the reagent solution.

11. The method of claim 8, wherein the reagent solution droplet further includes at least about 0.3 wt. % polyelectrolytes.

12. The method of claim 8, wherein the dried reagent has a uniformity in which the ratio of the thinnest point to the thickest point is greater than 0.3.

13. The method of claim 12, wherein the dried reagent has a uniformity in which the ratio of the thinnest point to the thickest point is greater than 0.4.

14. The method of claim 8, wherein the thickness of the dried reagent is from about 1 to about 5 micrometers (μm).

15. The method of claim 8, wherein the thickness of the dried reagent is from about 0.5 to about 5 micrometers (μm).

16. A method of forming an electrochemical test sensor, the method comprising:

providing a base and a lid;

forming a plurality of electrodes on at least one of the base and the lid;

dropping a reagent solution droplet so as to be in contact with at least one of the electrodes, the reagent solution droplet including an enzyme, a mediator, and a multivalent salt, the multivalent salt including sodium phosphate, the enzyme including flavin adenine dinucleotide-glucose dehydrogenase (FAD-GDH), the mediator including a 3-phenylimino-3H-phenothiazine or a 3-phenylimino-3H-phenoxazine; and drying the reagent solution droplet after placement thereof such that dried reagent has a uniformity in which the ratio of the thinnest point to the thickest point is greater than about 0.2, wherein the thickness of the dried reagent is from about 0.5 to about 20 micrometers (μm).

17. The method of claim 16, wherein the multivalent salt includes dibasic sodium phosphate.

18. The method of claim 16, further including a cellulose polymer, the cellulose polymer being hydroxyethyl cellulose.

19. The method of claim 16, wherein the thickness of the dried reagent is from about 1 to about 5 micrometers (μm).

20. The method of claim 16, wherein the thickness of the dried reagent is from about 0.5 to about 5 micrometers (μm).

* * * * *